US011197821B2

(12) United States Patent
Clark et al.

(10) Patent No.: US 11,197,821 B2
(45) Date of Patent: *Dec. 14, 2021

(54) FORMULATIONS FOR TREATMENT OF DRY EYE DISEASE

(71) Applicant: Aldeyra Therapeutics, Inc., Lexington, MA (US)

(72) Inventors: David Clark, Winchester, MA (US); Todd Brady, Carlisle, MA (US); Susan Macdonald, Danvers, MA (US); Stephen Gitu Machatha, Wilmington, MA (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 109 days.

This patent is subject to a terminal disclaimer.

(21) Appl. No.: 16/582,720

(22) Filed: Sep. 25, 2019

(65) Prior Publication Data

US 2020/0121591 A1 Apr. 23, 2020

Related U.S. Application Data

(60) Provisional application No. 62/736,417, filed on Sep. 25, 2018, provisional application No. 62/824,233, filed on Mar. 26, 2019.

(51) Int. Cl.
| | |
|---|---|
| *A61K 9/00* | (2006.01) |
| *A61K 31/47* | (2006.01) |
| *A61K 47/40* | (2006.01) |
| *A61K 9/08* | (2006.01) |
| *A61P 27/04* | (2006.01) |

(52) U.S. Cl.
CPC .............. *A61K 9/0048* (2013.01); *A61K 9/08* (2013.01); *A61K 31/47* (2013.01); *A61K 47/40* (2013.01); *A61P 27/04* (2018.01)

(58) Field of Classification Search
CPC ...... A61K 9/0048; A61K 31/47; A61K 47/40; A61K 9/08; A61P 27/04
USPC ........................................................ 514/313
See application file for complete search history.

(56) References Cited

U.S. PATENT DOCUMENTS

| | | | |
|---|---|---|---|
| 3,912,748 | A | 10/1975 | Evans et al. |
| 4,668,626 | A | 5/1987 | Kobayashi et al. |
| 4,956,351 | A | 9/1990 | Mesens et al. |
| 5,024,998 | A | 6/1991 | Bodor |
| 5,364,637 | A | 11/1994 | De et al. |
| 5,376,645 | A | 12/1994 | Stella et al. |
| 5,419,898 | A | 5/1995 | Ikejiri et al. |
| 5,472,954 | A | 12/1995 | Loftsson |
| 5,576,311 | A | 11/1996 | Guy |
| 5,668,117 | A | 9/1997 | Shapiro |
| 5,767,109 | A | 6/1998 | Sanchez et al. |
| 5,998,488 | A | 12/1999 | Shinohara et al. |
| 6,191,127 | B1 | 2/2001 | Holscher et al. |
| 6,444,221 | B1 | 9/2002 | Shapiro |
| 6,492,520 | B1 | 12/2002 | Chen |
| 6,525,056 | B2 | 2/2003 | Arvanitis et al. |
| 7,973,025 | B2 | 7/2011 | Jordan et al. |
| 7,982,071 | B2 | 7/2011 | Scott et al. |
| 8,158,609 | B1 | 4/2012 | Marsh et al. |
| 8,435,965 | B2 | 5/2013 | Tabuchi et al. |
| 8,722,669 | B2 | 5/2014 | Palczewski et al. |
| 8,791,154 | B2 | 7/2014 | Gamache et al. |
| 8,940,721 | B2 | 1/2015 | Jordan et al. |
| 9,259,427 | B2 | 2/2016 | Tierney et al. |
| 9,265,759 | B2 | 2/2016 | Jordan et al. |
| 9,364,471 | B2 | 6/2016 | Jordan et al. |
| 9,650,342 | B2 | 5/2017 | Jordan et al. |
| 9,814,701 | B2 | 11/2017 | Jordan et al. |
| 9,896,419 | B2 | 2/2018 | Jordan et al. |
| 10,202,348 | B2 | 2/2019 | Jordan et al. |
| 10,213,395 | B2 | 2/2019 | Brady et al. |
| 10,414,732 | B2 | 9/2019 | Buist et al. |
| 10,426,790 | B2 | 10/2019 | Young et al. |
| 10,543,181 | B2 | 1/2020 | Brady et al. |
| 10,550,085 | B2 | 2/2020 | Brady et al. |
| 10,588,874 | B2 | 3/2020 | Brady et al. |
| 10,913,722 | B2 | 2/2021 | Jordan et al. |
| 11,007,157 | B2 | 5/2021 | Brady et al. |
| 2004/0198828 | A1 | 10/2004 | Abelson et al. |
| 2005/0090553 | A1 | 4/2005 | Shapiro |
| 2005/0130906 | A1 | 6/2005 | Matier et al. |
| 2005/0234018 | A1 | 10/2005 | Lyons et al. |
| 2006/0111318 | A1 | 5/2006 | Okamoto |

(Continued)

FOREIGN PATENT DOCUMENTS

| | | |
|---|---|---|
| CN | 101321742 A | 12/2008 |
| CN | 104884049 A | 9/2015 |

(Continued)

OTHER PUBLICATIONS

Abelson et al., "Combined analysis of two studies using the conjunctival allergen challenge model to evaluate olopatadine hydrochloride, a new ophthalmic antiallergic agent with dual activity," American Journal of Ophthalmology, 1998; 125(6):797-804.

Abelson et al., "Conjunctival allergen challenge. A clinical approach to studying allergic conjunctivitis," Archives of Ophthalmology, 1990; 108(1):84-88.

Abelson et al., "Conjunctival allergen challenge: models in the investigation of ocular allergy," Current Allergy and Asthma Reports, 2003; 3(4):363-368.

Abelson et al., The conjunctival provocation test model of ocular allergy: utility for assessment of an ocular corticosteroid, loteprednol etabonate, J Ocul Pharmacol Ther, 1998; 14(6):533-42.

Ackerman et al., "Ocular itch associated with allergic conjunctivitis: latest evidence and clinical management," Ther. Adv. Chronic Dis., 2016; 7(1):52-67.

(Continued)

*Primary Examiner* — Tracy Vivlemore
*Assistant Examiner* — Ebenezer O Sackey
(74) *Attorney, Agent, or Firm* — Dechert LLP; Andrea L. C. Reid; Joseph W. Arico

(57) ABSTRACT

The present invention provides a reproxalap ophthalmic solution, and methods of using the same for treating dry eye disease.

24 Claims, 9 Drawing Sheets

(56) References Cited

U.S. PATENT DOCUMENTS

| | | |
|---|---|---|
| 2006/0257488 A1 | 11/2006 | Hubbard |
| 2010/0240624 A1 | 9/2010 | Chapin et al. |
| 2011/0105450 A1 | 5/2011 | Chapin et al. |
| 2011/0263645 A1 | 10/2011 | Jordan et al. |
| 2012/0108585 A1 | 5/2012 | Vu |
| 2012/0295967 A1 | 11/2012 | Gamache et al. |
| 2012/0302601 A1 | 11/2012 | Jordan et al. |
| 2013/0165419 A1 | 6/2013 | Lindstrom et al. |
| 2013/0190500 A1 | 7/2013 | Greiner et al. |
| 2014/0038918 A1 | 2/2014 | Rodriguez-Boulan et al. |
| 2014/0235604 A1 | 8/2014 | Palczewski et al. |
| 2017/0095449 A1 | 4/2017 | Winters et al. |
| 2018/0050989 A1 | 2/2018 | Machatha et al. |
| 2018/0092882 A1 | 4/2018 | Jordan et al. |
| 2018/0250306 A1 | 9/2018 | Brady et al. |
| 2019/0105322 A1 | 4/2019 | Macdonald et al. |
| 2019/0125729 A1 | 5/2019 | Chabala et al. |
| 2019/0183878 A1* | 6/2019 | Brady ............... A61K 9/0048 |
| 2019/0210971 A1 | 7/2019 | Jordan et al. |
| 2019/0247334 A1 | 8/2019 | Brady et al. |
| 2020/0038392 A1 | 2/2020 | Brady et al. |
| 2020/0062712 A1 | 2/2020 | Machatha et al. |
| 2020/0199075 A1 | 6/2020 | Brady et al. |
| 2020/0246345 A1 | 8/2020 | Brady et al. |
| 2020/0323841 A1* | 10/2020 | Clark ............... A61K 9/0048 |

FOREIGN PATENT DOCUMENTS

| | | | |
|---|---|---|---|
| CN | 105120866 A | 12/2015 | |
| EP | 2301549 A1 | 3/2011 | |
| EP | 1888548 B1 | 8/2012 | |
| JP | 06-239748 A | 8/1994 | |
| JP | 07-025758 A | 1/1995 | |
| JP | 09-169647 A | 6/1997 | |
| JP | 2001041757 | 6/2001 | |
| JP | 2002003364 | 1/2002 | |
| JP | 2002003364 A | 1/2002 | |
| JP | 2005-187407 A | 7/2005 | |
| JP | 2006-008568 A | 1/2006 | |
| JP | 3736916 | 1/2006 | |
| JP | 3736916 B2 | 1/2006 | |
| JP | 2007532648 A | 11/2007 | |
| JP | 4466875 | 5/2010 | |
| JP | 4466875 B2 | 5/2010 | |
| JP | 4748289 B2 | 8/2011 | |
| JP | 2012506449 A | 3/2012 | |
| JP | 5194218 | 5/2013 | |
| JP | 5194218 B2 | 5/2013 | |
| JP | 2014-515355 A | 6/2014 | |
| JP | 2015-057437 A | 3/2015 | |
| JP | 2015-535293 A | 12/2015 | |
| JP | 2016-508994 A | 3/2016 | |
| WO | WO-2001041757 A1 | 6/2001 | |
| WO | WO-2005105067 A2 | 11/2005 | |
| WO | WO-2006000421 A2 | 1/2006 | |
| WO | WO-2006002473 A1 | 1/2006 | |
| WO | WO-2006127945 A1 | 11/2006 | |
| WO | WO-2010048332 A2 | 4/2010 | |
| WO | WO-2011008202 A1 | 1/2011 | |
| WO | WO-2011071995 A2 | 6/2011 | |
| WO | WO-2011072141 A1 | 6/2011 | |
| WO | WO-2012105887 A1 | 8/2012 | |
| WO | WO-2014100425 A1 | 6/2014 | |
| WO | WO-2014116593 A1 | 7/2014 | |
| WO | WO-2014116836 A2 | 7/2014 | |
| WO | WO-2015002893 A1 | 1/2015 | |
| WO | WO-2015187942 A1 | 12/2015 | |
| WO | WO-2016085939 A2 | 6/2016 | |
| WO | WO-2017035077 A1 | 3/2017 | |
| WO | WO-2017035082 A1 | 3/2017 | |
| WO | WO-2017147617 A1 | 8/2017 | |
| WO | WO-2017196881 A1 | 11/2017 | |
| WO | WO-2018039192 A1 | 3/2018 | |
| WO | WO-2018039197 A1 | 3/2018 | |
| WO | WO-2018064354 A1 | 4/2018 | |
| WO | WO-2018170476 A1 | 9/2018 | |
| WO | WO-2019075136 A1 | 4/2019 | |
| WO | WO-2020018498 A1 | 1/2020 | |
| WO | WO-2020028820 A1 | 2/2020 | |
| WO | WO-2020033344 A1 | 2/2020 | |
| WO | WO-2020198064 A1 | 10/2020 | |
| WO | WO-2020223685 A1 | 11/2020 | |
| WO | WO-2020223717 A1 | 11/2020 | |

OTHER PUBLICATIONS

Al-Bari, "Chloroquine analogues in drug discovery: new directions of uses, mechanisms of actions and toxic manifestations from malaria to multifarious diseases," J Antimicrob Chemother. 2015;70(6):1608-21.

Aldeyra Press Release—Aldeyra Therapeutics Abstract Accepted at 2015 American Academy of Allergy Asthma & Immunology Annual Meeting, Dec. 16, 2014 (2 pages).

Aldeyra Press Release—Aldeyra Therapeutics Abstracts Accepted for Presentation at the 2015 Annual Meeting of the Association for Research in Vision and Ophthalmology, Feb. 2, 2015 (2 pages).

Aldeyra Press Release—Aldeyra Therapeutics Announces Clinical Development Update for Phase 3 Programs, Jan. 25, 2017 (2 pages).

Aldeyra Press Release—Aldeyra Therapeutics Announces First Patient Enrolled in Allergic Conjunctivitis Phase 2b Clinical Trial, Feb. 7, 2017 (2 pages).

Aldeyra Press Release—Aldeyra Therapeutics Announces First Patient Enrolled in Allergic Conjunctivitis Phase 3 Clinical Trial, Apr. 24, 2018 (2 pages).

Aldeyra Press Release—Aldeyra Therapeutics Announces First Patient Enrolled in Allergic Conjunctivitis Phase IIa Clinical Trial, Sep. 29, 2015 (2 pages).

Aldeyra Press Release—Aldeyra Therapeutics Announces First Patient Enrolled in Dry Eye Disease Phase 2a Clinical Trial, Jun. 6, 2017 (2 pages).

Aldeyra Press Release—Aldeyra Therapeutics Announces First Patient Enrolled in Dry Eye Disease Phase 2b Clinical Trial, Jan. 30, 2018 (2 pages).

Aldeyra Press Release—Aldeyra Therapeutics Announces First Patient Enrolled in Noninfectious Anterior Uveitis Phase 3 Clinical Trial, Apr. 27, 2017 (2 pages).

Aldeyra Press Release—Aldeyra Therapeutics Announces First Patient Enrolled in Noninfectious Anterior Uveitis Phase II Clinical Trial, Apr. 16, 2015 (2 pages).

Aldeyra Press Release—Aldeyra Therapeutics Announces Last Patient Dosed in Dry Eye Disease Phase 2a Clinical Trial, Jul. 18, 2017 (2 pages).

Aldeyra Press Release—Aldeyra Therapeutics Announces Last Patient Dosed in Dry Eye Disease Phase 2b Clinical Trial, Jul. 12, 2018 (2 pages).

Aldeyra Press Release—Aldeyra Therapeutics Announces Last Patient Dosed in Phase II Trial of NS2 in Patients with Allergic Conjunctivitis, Dec. 16, 2015 (2 pages).

Aldeyra Press Release—Aldeyra Therapeutics Announces Last Patient Dosed in the ALLEVIATE Phase 3 Clinical Trial, Dec. 20, 2018 (2 pages).

Aldeyra Press Release—Aldeyra Therapeutics Announces Positive Results from Dry Eye Disease Phase 2a Clinical Trial, Sep. 12, 2017 (3 pages).

Aldeyra Press Release—Aldeyra Therapeutics Announces Positive Results from Phase 2b Dry Eye Disease Clinical Trial, Sep. 26, 2018 (2 pages).

Aldeyra Press Release—Aldeyra Therapeutics Announces Positive Top-Line Results from the Phase 3 ALLEVIATE Trial in Patients with Allergic Conjunctivitis, Mar. 26, 2019 (2 pages).

Aldeyra Press Release—Aldeyra Therapeutics Announces Presentation of Phase 2 Allergic Conjunctivitis Results at the 2016 American College of Allergy, Asthma and Immunology Annual Scientific Meeting, Nov. 7, 2016 (2 pages).

Aldeyra Press Release—Aldeyra Therapeutics Announces Presentation of Results on the Efficacy of ADX-102 in Noninfectious

(56) References Cited

OTHER PUBLICATIONS

Anterior Uveitis at the American Uveitis Society Held at the American Academy of Ophthalmology 2017 Annual Meeting, Oct. 25, 2017 (2 pages).
Aldeyra Press Release—Aldeyra Therapeutics Announces Results from Allergic Conjunctivitis Phase 2b Clinical Trial and Plans for Phase 3 Clinical Testing, Jun. 14, 2017 (3 pages).
Aldeyra Press Release—Aldeyra Therapeutics Announces Third Quarter 2017 Financial Results, Nov. 9, 2017 (4 pages).
Aldeyra Press Release—Aldeyra Therapeutics Opens Enrollment in Noninfectious Anterior Uveitis Phase II Clinical Trial, Mar. 26, 2015 (2 pages).
Aldeyra Press Release—Aldeyra Therapeutics Opens Enrollment in Sjogren-Larsson Syndrome Clinical Trial and Finalizes Noninfectious Anterior Uveitis Clinical Trial Protocol, Mar. 17, 2015 (2 pages).
Aldeyra Press Release—Aldeyra Therapeutics Presents Dry Eye Disease Phase 2a Clinical Trial Results at the Association for Research in Vision and Ophthalmology 2018 Annual Meeting, May 1, 2018 (2 pages).
Aldeyra Press Release—Aldeyra Therapeutics Presents Noninfectious Anterior Uveitis Phase 2 Clinical Trial Data at the Association for Research in Vision and Ophthalmology 2017 Annual Meeting, May 17, 2017 (3 pages).
Aldeyra Press Release—Aldeyra Therapeutics Presents Noninfectious Anterior Uveitis Phase 2 Clinical Trial Data to the American Uveitis Society Held at the American Academy of Ophthalmology 2017 Annual Meeting, Nov. 29, 2017 (2 pages).
Aldeyra Press Release—Aldeyra Therapeutics Provides Update on Late-Stage Clinical Trials at 2016 Research and Development Day, Sep. 26, 2016 (2 pages).
Aldeyra Press Release—Aldeyra Therapeutics Provides Update on NS2 Clinical Program, Mar. 2, 2015 (2 pages).
Aldeyra Press Release—Aldeyra Therapeutics Provides Update on Ophthalmic Programs at 2019 Research & Development Day, Feb. 28, 2019 (2 pages).
Aldeyra Press Release—Aldeyra Therapeutics Reaches Agreement with the US Food and Drug Administration for the Use of RASP as an Objective Sign for the Treatment of Dry Eye Disease, Jun. 4, 2020 (2 pages).
Aldeyra Press Release—Aldeyra Therapeutics Schedules Conference Call and Webcast to Announce Results from Allergic Conjunctivitis Phase 2b Clinical Trial, Jun. 13, 2017 (1 page).
Aldeyra Press Release—Aldeyra Therapeutics Schedules Webcast and Conference Call to Announce Results from Dry Eye Disease Phase 2a Clinical Trial, Sep. 11, 2017 (1 page).
Aldeyra Press Release—Aldeyra Therapeutics Selected for Podium Presentation of Phase 2a Dry Eye Disease Results at the 2018 Association for Research in Vision and Ophthalmology (ARVO) Annual Meeting, Feb. 21, 2018 (3 pages).
Aldeyra Press Release—Aldeyra Therapeutics Submits FDA IND Filing for Noninfectious Anterior Uveitis, Dec. 18, 2014 (2 pages).
Aldeyra Press Release—Aldeyra Therapeutics to Host 2019 Research & Development Day, Feb. 12, 2019 (1 page).
Aldeyra Press Release—Aldeyra Therapeutics' Data on Lead Candidate NS2 to be Presented at Society for Investigative Dermatology 2014 Annual Meeting, May 8, 2014 (2 pages).
Aldeyra Press Release—Aldeyra Therapeutics, Inc. Announces Last Patient Dosed in Allergic Conjunctivitis Phase 2b Clinical Trial, Apr. 18, 2017 (2 pages).
Aldeyra Press Release—Positive Results From Phase II Clinical Trial in Subjects With Noninfectious Anterior Uveitis, May 9, 2016 (4 pages).
Aldeyra Press Release—Phase II Allergic Conjunctivitis, Feb. 29, 2016 (3 pages).
Aldini et al., "Lipoxidation-Derived Reactive Carbonyl Species as Potential Drug Targets in Preventing Protein Carbonylation and Related Cellular Dysfunction," ChemMedChem, 2006; 1(10):1045-1058.

Amara et al., "Autoantibodies to malondialdehyde-modified epitope in connective tissue disease and vasculitides," Clinical and Experimental Immunology, 1995; 101(2):233-238.
Ao et al., "Methyl-β-Cyclodextrin Impairs the Monocyte-Adhering Ability of Endothelial Cells by Down-Regulating Adhesion Molecules and Caveolae and Reorganizing the Actin Cytoskeleton," Biol Pharm Bull, 2016; 39(6):1029-1034.
Augustin et al., "Oxidative reactions in the tear fluid of patients suffering from dry eyes," Graefe's Archive for Clinical and Experimental Ophthalmology, 1995; 233(11):694-698.
Bacsi et al., "Effect of pollen-mediated oxidative stress on immediate hypersensitivity reactions and late-phase inflammation in allergic conjunctivitis," J. Allergy Clin. Immunol., 2005; 116(4):836-843.
Badii, "Allergic Conjunctivitis," https://www.healthline.com/health/allergic-conjunctivitis, Apr. 28, 2016 (12 pages) [retrieved on Nov. 22, 2019].
Balci et al., "Effects of computer monitor-emitted radiation on oxidant/antioxidant balance in cornea and lens from rats," Molec Vis, 2009; 15:2521-2525.
Balci et al., "Investigation of oxidative stress in pterygium tissue," Molecular Vision, 2011; 17:443-447.
Baltatzis et al., "Mycophenolate mofetil as an immunomodulatory agent in the treatment of chronic ocular inflammatory disorders," Ophthalmology, 2003; 110(5):1061-5.
Boldogh et al., "ROS generated by pollen NADPH oxidase provide a signal that augments antigen-induced allergic airway inflammation," J. Clin. Invest., 2005; 115(8):2169-2179.
Boyer et al., "Lipofuscin and N-Retinylidene-N-Retinylethanolamine (A2E) Accumulate in Retinal Pigment Epithelium in Absence of Light Exposure," J Biol Chem, 2012; 287(26):22276-22286.
Bozkir et al., "Effect of hydroxypropyl-beta-cyclodextrin on the solubility, stability and in-vitro release of ciprofloxacin for ocular drug delivery," Acta Poloniae Pharmaceutica, 2012; 69(4):719-24.
Bragagni et al., "Cyclodextrin complexation highly enhances efficacy of arylsulfonylureido benzenesulfonamide carbonic anhydrase inhibitors as atopical antiglaucoma agents," Bioorganic & Medicinal Chemistry, 2015; 23(18):6223-6227.
Brewitt et al., "Dry Eye Disease—The Scale of the Problem," Survey of Ophthalmol, 2001; 45(Suppl 2):S199-S2.
BRIDION® (sugammadex) Injection Prescribing Information, for intravenous use, Initial U.S. Approval: 2015, Last Revised Dec. 2015 (19 pages).
Brozek et al., "Grading quality of evidence and strength of recommendations in clinical practice guidelines: Part 2 of 3. The GRADE approach to grading quality of evidence about diagonstic tests and strategies," Allergy, 2009; 64(8):1109-1116.
Buddi et al., "Evidence of oxidative stress in human corneal diseases," The Journal of Histochemistry and Cytochemistry: official journal of the Histochemistry Society, 2002; 50(3):341-351.
Burcham et al., "Aldehyde-Sequestering Drugs: Tools for Studying Protein Damage by Lipid Peroxidation Products," Toxicology, 2002; 181-182:229-236.
Burstein, "Preservative cytotoxic threshold for benzalkonium chloride and chlorhexidine digluconate in cat and rabbit corneas," Investigative Ophthalmology and Visual Science, 1980; 19(3):308-313.
Burstein, "The effects of topical drugs and preservatives on the tears and corneal epithelium in dry eye," Transactions of the Ophthalmological Societies of the United Kingdom, 1985; 104:402-409.
Canonica et al., "Recommendations for standardization of clinical trials with Allergen Specific Immunotherapy for respiratory allergy. A statement of a World Allergy Organization (WAO) taskforce," Allergy, 2007; 62(3):317-324.
Cejkova et al., "The role of conjunctival epithelial cell xanthine oxidoreductase/xanthine oxidase in oxidative reactions on the ocular surface of dry eye patients with Sjögren's syndrome," Histol Histopathol 2007; 22(9):997-1003.
Chapple et al., "Unfolding Retinal Dystrophies: a Role for Molecular Chaperones?" Trends Mol Med, 2001; 7(9):414-421.
Chen et al., "Methazolamide Calcium Phosphate Nanoparticles in an Ocular Delivery System," Pharm Soc Japan, 2010; 130(3):419-24.

(56) References Cited

OTHER PUBLICATIONS

Choi et al., "Expression of Lipid Peroxidation Markers in the Tear Film and Ocular Surface of Patients with Non-Sjogren Syndrome: Potential Biomarkers for Dry Eye Disease," Curr Eye Res, 2016; 41(9):1143-11.
Ciolino et al., "Effect of alcaftadine 0.25% on ocular itch associated with seasonal or perennial allergic conjunctivitis: a pooled analysis of two multicenter randomized clinical trials," Clin Ophthalmol, 2015; 9:765-72.
Clinical Trials Results for Outcome Measures of Ocular Itching and Ocular Tearing (1 page) (2016).
Clinical Trials Results of Treatment with Aldehyde Trapping Compound NS2 (1 page) (2015).
Clinical Trials Results of Treatment with NS2 Topical Formulation (1 page) (2015).
ClinicalTrials.gov identifier NCT02406209, "A Safety and Efficacy Study of NS2 in Patients with Anterior Uveitis," https://clinicaltrials.gov/ct2/show/NCT02406209 (4 pages) (2015).
ClinicalTrials.gov identifier NCT02578914, "A Safety and Activity Study of NS2 in Subjects with Allergic Conjunctivitis," https://clinicaltrials.gov/ct2/show/NCT02578914 (6 pages) (2015).
ClinicalTrials.gov identifier NCT03162783, "A Randomized, Double Masked, Clinical Study of Subjects with Dry Eye Syndrome," (7 pages) (2017).
Cullen et al., "The small molecule aldehyde trap NS2 exhibits potent anti-inflammatory activity in three murine models of inflammation," AAAAI Annual Meeting Abstract, 1 page (Feb. 2015).
Davies, "Biopharmaceutical considerations in topical ocular drug delivery," Clin Exp Pharmacol Physiol, 2000; 27(7):558-62.
Del Valle, "Cyclodextrins and their uses: a review," Process Biochemistry, 2004; 39(9):1033-1046.
Demir et al., "Oxidative stress of intracameral lidocaine and levobupivacaine on ocular tissues," Br J Ophthalmol, 2010; 94(8):1083-7.
Demir et al., "The protective effect of alpha-lipoic acid against oxidative damage in rabbit conjunctiva and cornea exposed to ultraviolet radiation," Ophthalmologica, 2005; 219(1):49-53.
Devillier et al., "The allergen challenge chamber: A valuable tool for optimizing the clinical development of pollen immunotherapy," Allergy, 2011; 66(2):163-9.
Division of AIDS, National Institute of Allergy and Infectious Diseases, National Institutes of Health, US Department of Health and Human Services, Division of AIDS (DAIDS) Table for Grading the Severity of Adult and Pediatric Adverse Events, V2.0, 33 pages. (Nov. 2014).
Esterbauer et al., "Chemistry and Biochemistry of 4-Hydroxynonenal, Malonaldehyde and Related Aldehydes," Free Radic Biol Med, 1991; 11:81-128.
European Supplementary Partial Search Report issued by the European Patent Office for European Patent Application No. 13865015.5 dated Mar. 31, 2016 (9 pages).
European Supplementary Partial Search Report issued by the European Patent Office for European Patent Application No. 14743711.5 dated Jul. 20, 2016 (14 pages).
Everest-Todd, "Topical Application of Cyclodextrin Ethers in the Control of Pain," Proceedings of the Eighth International Symposium on Cyclodextrins, pp. 495-498 (1998).
FDA, "BAM R59: Phosphate-Buffered Saline (PBS), pH 7.4," Jan. 2001, retrieved online at <http://www.fda.gov/Food/FoodScienceR.esearch/LaboratoxyMethods/ucm062268.htm> on Apr. 18, 2015 (1 page).
Gasper et al., "2-Hydroxypropyl-beta-cyclodextrin (HPβCD) reduces age-related lipofuscin accumulation through a cholesterol-associated pathway," Scientific Reports, 2017; 7(2197):1-7.
Gibson et al., "The Aldehyde Trap NS2 Mitigates Dense Haze in a Rabbit Model of Photorefractive Keratectomy" ARVO Annual Meeting Abstract, 1 page (Jun. 2015).

Goldstein et al., "A Phase 2 Exploratory Study of a Novel Interleukin-1 Receptor Inhibitor (EBI-005) in the Treatment of Moderate-to-Severe Allergic Conjunctivitis," Eye Contact Lens, 2015; 41(3):145-55.
Green et al., "Influence of Various Agents on Corneal Permeability," American Journal of Ophthalmology, 1971; 72(5):897-905.
Grotto et al., "Importance of the lipid peroxidation biomarkers and methodological aspects for malondialdehyde quantification," Quim Nova, 2009; 32(1):169-174.
Herbort et al., "Endotoxin-induced uveitis in the rat," Graefe's Arch Clin Exp Ophthalmol, 1988; 226:553-8.
Hessen et al., "Dry Eye: an Inflammatory Ocular Disease," J Ophthalmic Vis Res, 2014; 9(2):240-250.
Hom et al., "Allergic conjunctivitis and dry eye syndrome," Ann Allergy Asthma Immunol, 2012; 108(3):163-6.
International Preliminary Report on Patentability issued by the United States Patent and Trademark Office as International Searching Authority for International Application No. PCT/US2014/012762 dated Jul. 28, 2015 (8 pages).
International Search Report and Written Opinion issued by the European Patent Office as International Searching Authority for International Patent Application No. PCT/US2019/044929 dated Nov. 20, 2019 (15 pages).
International Search Report and Written Opinion issued by the United States Patent and Trademark Office as International Searching Authority for International Application No. PCT/US2010/059719 dated Feb. 8, 2011 (7 pages).
International Search Report and Written Opinion issued by the United States Patent and Trademark Office as International Searching Authority for International Application No. PCT/US2014/012762 dated Jul. 18, 2014 (11 pages).
International Search Report and Written Opinion issued by the United States Patent and Trademark Office as International Searching Authority for International Application No. PCT/US2017/047945 dated Oct. 20, 2017 (9 pages).
International Search Report and Written Opinion issued by the United States Patent and Trademark Office as International Searching Authority for International Patent Application No. PCT/US2017/020020 dated May 24, 2017 (12 pages).
International Search Report and Written Opinion issued by the United States Patent and Trademark Office as International Searching Authority for International Patent Application No. PCT/US2017/031808 dated Aug. 11, 2017 (10 pages).
International Search Report and Written Opinion issued by the United States Patent and Trademark Office as International Searching Authority for International Patent Application No. PCT/US2017/047958 dated Oct. 31, 2017 (10 pages).
International Search Report and Written Opinion issued by the United States Patent and Trademark Office as International Searching Authority for International Patent Application No. PCT/US2018/023000 dated Jun. 1, 2018 (8 pages).
International Search Report and Written Opinion issued by the United States Patent and Trademark Office as International Searching Authority for International Patent Application No. PCT/US2018/055310 dated Jan. 29, 2019 (9 pages).
International Search Report and Written Opinion issued by the United States Patent and Trademark Office as International Searching Authority for International Patent Application No. PCT/US2019/041942 dated Sep. 30, 2019 (18 pages).
International Search Report and Written Opinion issued by the United States Patent and Trademark Office as International Searching Authority for International Patent Application No. PCT/US2019/054263, dated Jan. 6, 2020 (13 pages).
International Search Report and Written Opinion issued by the United States Patent and Trademark Office as International Searching Authority for International Patent Application No. PCT/US2019/169097, dated Dec. 10, 2019 (11 pages).
International Search Report and Written Opinion issued by the United States Patent and Trademark Office as International Searching Authority for International Patent Application No. PCT/US2020/024022, dated Jun. 17, 2020 (11 pages).
International Search Report and Written Opinion issued by the United States Patent and Trademark Office as International Search-

(56) References Cited

OTHER PUBLICATIONS ing Authority for International Patent Application No. PCT/US2020/031138, dated Jul. 13, 2020 (7 pages).
International Search Report and Written Opinion issued by the United States Patent and Trademark Office as International Searching Authority for International Patent Application No. PCT/US2020/031219, dated Aug. 31, 2020 (14 pages).
Jacobs et al., "Responses to ragweed pollen in a pollen challenge chamber versus seasonal exposure identify allergic rhinoconjunctivitis endotypes," J. Allergy Clin. Immunol., 2012; 130(1):122-7.
Johannsdottir et al., "Development of a Cyclodextrin-Based Aqueous Cyclosporin A Eye Drop Formulations," International Journal of Pharmaceutics, 2015; 493(1-2):86-95.
Johnson et al., "2-Hydroxypropyl-β-Cyclodextrin Removes All-Trans Retinol from Frog Rod Photoreceptors in a Concentration-Dependent Manner," Journal of Ocular Pharmacology and Therapeutics, 2010; 26(3):245-248.
Kam et al., "Topical Cyclodextrin Reduces Amyloid Beta and Inflammation Improving Retinal Function in Ageing Mice," Experimental Eye Research, 2015; 135:59-66.
Knapp et al., "Intraocular Availability of Topically Applied Mycophenolate Mofetil in Rabbits," J. Ocul. Pharmacol. Ther., 2003; 19(2):181-192.
La Rosa et al., "Allergic conjunctivitis: a comprehensive review of the literature," Ital J Pediatr, 2013; 39:18.
Leonardi et al., "Correlation Between Conjunctival Provocation Test (CPT) and Systemic Allergometric Tests in Allergic Conjunctivitis," Eye, 1990; 4:760-764.
Leonardi, "Allergy and allergic mediators in tears," Exp. Eye Res., 2013; 117:106-17.
Liang et al., "Ocular safety of cationic emulsion of cyclosporine in an in vitro corneal wound-healing model and an acute in vivo rabbit model," Mol Vis, 2012; 18:2195-204.
Loftsson et al., "Cyclodextrin Microparticles for Drug Delivery to the Posterior Segment of the Eye: Aqueous Dexamethasone Eye Drops," Journal of Pharmacy and Pharmacology, 2007; 59(5):629-635.
Loftsson et al., "Cyclodextrins in Eye Drop Formulations: Enhanced Topical Delivery of Corticosteroids to the Eye," Acta Ophthalmologica Scandinavica, 2002; 80(2):144-150.
Lopachin et al., "Molecular mechanisms of aldehyde toxicity: a chemical perspective," Chem Res Toxicol, 2014; 27(7):1081-91.
Macdonald et al., "ADX-102, a novel aldehyde trap, reduces nociceptive behavior in mouse models of carrageenan and CFA induced pain," Int'l Conference on Pain Research & Management Abstract, J Pain Relief, 5 (5 Suppl):50 (Oct. 2016).
Macdonald et al., "Inhibition of fibroblast activation to the myofibroblast phenotype in neonatal rat cardiac fibroblasts using a small molecule aldehyde trap," ASCB Annual Meeting Abstract, p. 2 (Dec. 2016).
Macdonald et al., "Novel Small Molecule Aldehyde Sequestering Agents Demonstrate Broad Therapeutic Potential for Ocular Inflammation," ARVO Annual Meeting Abstract, 2 pages (Jul. 2018).
Macdonald et al., "The novel aldehyde trap, ADX-102, reduces inflammation-mediated lung infilrate in a mouse model of LPS-induced acute lung injury," 13th World Congress on Inflammation Abstract, p. 192 (Jul. 2017).
Maeda et al., "Primary amines protect against retinal degeneration in mouse models of retinopathies," Nat Chem Biol, 2011; 8(2):170-178.
Mandell et al., "The Aldehyde Trap NS2 Reduces Ocular Inflammation in an Endotoxin-Induced Model in Rats," ARVO Annual Meeting Abstract, 2 pages (Jun. 2015).
Maurice et al., "Advances in targeting cyclic nucleotide phosphodiesterases," Nat Rev Drug Discov., 2014; 13:290-314.
McCord et al., "Superoxide dismutase. An enzymic function for erythrocuprein (hemocuprein).," J. Biol. Chem., 1969; 244: 6049-6055.
McLaurin et al., "Phase 3 Randomized Double-Masked Study of Efficacy and Safety of Once-Daily 0.77% Olopatadine Hydrochloride Ophthalmic Solution in Subjects with Allergic Conjunctivitis Using the Conjunctival Allergen Challenge Model," Clinical Science, 2015; 34(10):1245-1251.
Mishra et al., "Recent Patents and Emerging Therapeutics in the Treatment of Allergic Conjunctivitis," Recent Pat. Inflamm. Allergy Drug Discov.; 2011; 5(1):26-36.
Nagai et al., Improved corneal toxicity and permeability of tranilast by the preparation of ophthalmic formulations containing its nanoparticles, J Oleo Sci, 2014; 63(2):177-86.
Nakamura et al., "Involvement of Oxidative Stress on Corneal Epithelial Alterations in a Blink-Suppressed Dry Eye," Investigative Ophthalmology and Visual Science, 2007; 48(4):1552-1558.
Negre-Salvayre et al., "Advanced Lipid Peroxidation End Products in Oxidative Damage to Proteins. Potential Role in Diseases and Therapeutic Prospects for the Inhibitors," Br J Pharmacol, 2008; 153(1):6-20.
Niwa et al., "Protein oxidative damage in the stratum corneum: Evidence for a link between environmental oxidants and the changing prevalence and nature of atopic dermatitis in Japan," Br J Dermatol., 2003; 149:248.
Nociari et al., "Beta cyclodextrins bind, stabilize, and remove lipofuscin bisretinoids from retinal pigment epithelium," Proc Natl Acad Sci U.S.A., 2014; E1402-E1408.
O'Brien et al., "Aldehyde Sources, Metabolism, Molecular Toxicity Mechanisms, and Possible Effects on Human Health," Crit Rev Toxicol, 2005; 35:609-662.
Pfaar et al., "Perspectives in allergen immunotherapy: 2017 and beyond," Allergy, 2018; 73(Suppl 104):5-23.
Pontikis et al., "Cyclodextrin alleviates neuronal storage of cholesterol in Niemann-Pick C disease without evidence of detectable blood-brain barrier permeability," Journal of Inherited Metabolic Disease, 2013; 36(3):491-498.
Pred Forte Prescribing Information, Allergan, 5 pages (2017).
Pubchem, 1824609-67-7, SID 333824451, Apr. 24, 2017 (6 pages).
Pubchem, 2-(3-Aminoquinolin-2-yl)propan-2-ol, CID 117758222, Feb. 23, 2016, modified Jun. 13, 2020 (11 pages).
Pubchem, Schembl16316728, CID 117758222, Feb. 23, 2016, modified Sep. 30, 2017 (13 pages).
Rajewski et al., "Pharmaceutical applications of cyclodextrins. 2. In vivo drug delivery," J Pharm Sci, 1996; 85(11):1142-69.
Rauli et al., "Validation of Malondialdehyde and 4-Hydroxy-2-trans-Nonenal Measurement in Plasma by NICI-GC-MS1," J Biochem., 1998; 123:918-923.
Restasis® Prescribing Information, Allergan, copyright 2016, revised 2017 (15 pages).
Rizzo et al., "Aldehyde Trapping Agent NS2 Blocks Formation of Fatty Aldehyde Adducts with Phosphatidylethanolamine and Suggests Potential Therapeutic Approach for Sjogren-Larsson Syndrome," Mol Genet and Metab, 114(3):362A (Mar. 2015) [Abstract Only].
Rizzo et al., "Endogenous antioxidants and radical scavengers," Advances in Experimental Medicine and Biology, 2010; 698:52-6.
Rizzo, Fatty aldehyde and fatty alcohol metabolism: review and importance for epidermal structure and function, Biochim Biophys Acta, 2014; 1841(3):377-89.
Roat, "Allergic Conjunctivitis," Merck Manual Professional Version, 3 pages (2016), Available at: https://www.merckmanuals.com/professional/eye-disorders/conjunctival-and-scleral-disorders/allergic-conjunctivitis.
Roat, "Scleritis," Merck Manual Professional Version, 3 pages (2016), Available at: https://www.merckmanuals.com/professional/eye-disorders/conjunctival-and-scleral-disorders/scleritis.
Rønborg et al., "Exposure chamber for allergen challenge. The development and validation of a new concept," Allergy, 1996; 51(2):82-8.
Sanchez et al., "Allergic Conjunctivitis," J Investig Allergol Clin Immunol., 2011; 21(2):1-19.
Sandikci et al., "Lipid Peroxidation and Antioxidant Defence System in Patients with Active or Inactive Behcet's Disease," Acta Derm Venereol, 2003; 83:342-346.
Sasaki et al., "Retinal drug delivery using eyedrop preparations of poly-L-lysine-modified liposomes," Eur J Pharm Biopharm, 2013; 83(3):364-9.

(56) References Cited

OTHER PUBLICATIONS

Satici et al., "Malondialdehyde and antioxidant enzyme levels in the aqueous humor of rabbits in endotoxin-induced uveitis," Eur J Ophthalmol, 2003; 13(9-10):779-83.
Schaumberg et al., "Epidemiology of dry eye syndrome," Lacrimal Gland, Tear Film, and Dry Eye Syndromes 3, Kluwer Academic/Plenum Publishers, pp. 989-998 (2002).
Schaumberg et al., "Prevalence of Dry Eye Disease among US Men: Estimates from the Physicians' Health Studies," Arch Ophthalmol, 2009; 127(6):763-768.
Schaumberg et al., "Prevalence of Dry Eye Syndrome Among US Women," Am J Ophthalmol, 2003; 136(2):318-326.
Search Report and Written Opinion issued by the Intellectual Property Office of Singapore for Singapore Patent Application No. 11201504859Y dated Aug. 1, 2016 (12 pages).
Sheppard et al., Targeting Anterior Uveitis: A Focus on Iontophoresis and Other Advanced Technologies, Sep. 1, 2018 [Retrieved Nov. 11, 2019] Retrieved from Internet URL: https://www.nyee.edu/files/NYEE/Health%20Professionals/Continuing%20Medical%20Education/Enduring%20CME%20Activities/158 _ supplernent. smaU_ v 1 _FINAL %20082818.pdf (8 pages).
Singh et al., "The epidemiology of ocular and nasal allergy in the United States, 1988-1994," J. Allergy Clin. Immunol., 2010; 126(4):778-783.
Smith et al., "Basic pathogenic mechanisms operating in experimental models of acute anterior uveitis," Immunol Cell Biol, 1998; 76:497-512.
Stevenson et al., "Dry eye disease: an immune-mediated ocular surface disorder," Arch Ophthalmol. 2012; 130(1): 90-100.
Study showing effect of ADX-102 on Fibrotic Changes in Cardiac Fibroblasts Following Cell Stress, American Society for Cell Biology Annual Meeting, Dec. 3-7, 2016 (2 pages).
Tang-Liu et al., "Effects of four penetration enhancers on corneal permeability of drugs in vitro," Journal of Pharmaceutical Sciences, 1994; 83(1):85-90.
Tempest-Roe et al., "Local therapies for inflammatory eye disease in translation: past, present and future," BMC Ophthalmol., 2013; 13(1):39.
Tukozkan et al., "Measurement of Total Malondialdehyde in Plasma and tissues by High-Performance Liquid Chromatography and Thiobarbituric Acid Assay," Firat Tip Dergisi, 2006; 11(2):88-92.
Turk et al., "Serum anti-carbonic anhydrase antibodies and oxidant-antioxidant balance in patients with acute anterior uveitis," Ocul Immunol Inflamm, 22(2):127-32 (Apr. 2014).
U.S. Appl. No. 16/547,930 of Buist et al., filed Aug. 22, 2019.
U.S. Appl. No. 16/773,654, filed Jan. 27, 2020.
U.S. Appl. No. 16/825,898, filed Mar. 20, 2020.
Ueda et al., "Evaluation of a Sulfobutyl Ether 13-Cyclodextrin as a Solubilizing/Stabilizing Agent for Several Drugs," Drug Dev Ind Pharm, 1998; 24(9):863-867.
Voziyan et al., "A Post-Amadori Inhibitor Pyridoxamine also Inhibits Chemical Modification of Proteins by Scavenging Carbonyl Intermediates for Carbohydrate and Lipid Degradation," J Biol Chem, 2002; 277(5):3397-3403.
Wakamatsu et al., "Evaluation of lipid oxidative stress status and inflammation in atopic ocular surface disease," Mol Vis, 2010; 16:2465-75.
Wood et al., "The concept of "aldehyde load" in neurodegenerative mechanisms: cytotoxicity of the polyamine degradation products hydrogen peroxide, acrolein, 3-aminopropanal, 3-acetamidiorioanal and 4-aminobutanal in a retinal ganglion cell line," Brain Research, 2007; 1145:150-156.
Yadav et al., "Regulation of NF-κB-Induced Inflammatory Signaling by Lipid Peroxidation-Derived Aldehydes," Oxidative Med & Cell Longev, 2013, Art ID 690545, 11 pages (2013).
Zarkovic "4-hydroxynonenal and neurodegenerative diseases," Molecular Aspects of Medicine, 2003; 24(4-5):293-303.
Zhou et al., "Mechanisms for the induction of HNE- MDA- and AGE-adducts, RAGE and VEGF in retinal pigment epithelial cells," Exp Eye Res., 2005; 80(4):567-80.
Sheppard et al., "A Randomized, Comparator-Controlled Phase 2 Clinical Trial of ADX-102 Ophthalmic Solution in Noninfectious Anterior Uveitis," ARVO Annual Meeting Abstract, Invest Ophth Vis Sci. 2017; 58(8):1231.

\* cited by examiner

FORMULATIONS FOR TREATMENT OF DRY EYE DISEASE

CROSS-REFERENCE TO RELATED APPLICATIONS

This application claims the benefit under 35 U.S.C. § 119(e) of U.S. Provisional Application No. 62/736,417, filed Sep. 25, 2018, and U.S. Provisional Application No. 62/824,233, filed Mar. 26, 2019; the entire contents of each of which is incorporated herein by reference.

TECHNICAL FIELD

The present invention relates to ophthalmic solutions comprising reproxalap, or a pharmaceutically acceptable salt thereof, for treatment of dry eye disease (DED).

BACKGROUND

Dry eye disease is a complex disease that results in ocular discomfort, visual disturbance, and tear film instability, which create the potential for damage to the ocular surface. It is characterized by increased osmolarity of the tear film and inflammation of the ocular surface. Estimates of the prevalence of dry eye disease vary considerably, depending on the criteria used to define the disease, but in the United States (U.S.), it has been estimated that as many as 20 million adults in the U.S. have dry eye disease. It has been projected that there will be a 40% increase in number of patients affected by 2030 (Schaumberg, Advances in Experimental Medicine and Biology, 2002, 506:989-98; Schaumberg, American Journal of Ophthalmology, 2003, 136:318-26; Schaumberg, Archives of Ophthalmology, 2009, 127: 763-8). With the aging population in the U.S. and other countries of the developed world, and increasing computer use, dry eye disease is expected to become more prevalent. Thus, finding a treatment is becoming more important (Brewitt, Survey of Ophthalmology, 2001, 45 Suppl 2:S199-202).

Aldehydes are reactive organic molecules that bind to proteins, carbohydrates, lipids and nucleic acids (Esterbauer, Free Radical Biology and Medicine, 1991, 11(1):81-128). Free aldehydes—aldehydes not sequestered or otherwise protected in specific metabolic processes—can be toxic, and aldehyde binding to cellular constituents can lead to inflammation (Yadav, Oxidative Medicine and Cellular Longevity, 2013, Volume 2013, Article ID 690545), molecular dysfunction (O'Brien, Critical Reviews in Toxicology, 2005, 35(7): 609-62), and the accumulation of indigestible metabolites, such as lipofuscin components in the retina (Boyer, J Biol Chem., 2012, 287:22276-86).

In biological systems, aldehydes are formed by a variety of processes, including the oxidation of alcohols, polyamine and glucose metabolism, and oxidative stress. In some disease states, aldehyde concentrations may be increased. Increases in aldehyde concentrations, particularly malonyldialdehyde (MDA), which is thought to he most commonly derived from lipid peroxidation, has been described in a variety of inflammatory ocular diseases, including pterygium, Behcet's Disease, Sjögren's Syndrome, anterior uveitis, and dry eye disease (Sandikci, Acta Dermato-Venereologica, 2003, 83(5): 342-6; Cejkova, Histology and Histopathology, 2007, 22(9):997-1003; Balci, Molecular Vision, 2011, 17: 443-7; Turk, Ocular Immunology and inflammation, 2014, 22(2):127-32; Choi, Current Eye Research, 2016, 41(9): 1143-9).

SUMMARY

In some embodiments, the present invention provides an ophthalmic solution comprising reproxalap, or a pharmaceutically acceptable salt thereof, and a pharmaceutically acceptable excipient, wherein the concentration of reproxalap, or a pharmaceutically acceptable salt thereof, is about 0.5% w/v or less and about 0.1% w/v or greater. In some embodiments, the ophthalmic solution comprises about 0.15 to 0.45% w/v reproxalap, or a pharmaceutically acceptable salt thereof, and a pharmaceutically acceptable excipient. In some embodiments, the ophthalmic solution comprises about 0.2 to 0.3% w/v reproxalap, or a pharmaceutically acceptable salt thereof, and a pharmaceutically acceptable excipient.

In some embodiments, the ophthalmic solution comprises about 0.25% w/v reproxalap, and a pharmaceutically acceptable excipient.

In some embodiments, the pharmaceutically acceptable excipient comprises a cyclodextrin, particularly sulfobutylether-$\beta$-cyclodextrin or hydroxypropyl-$\beta$-cyclodextrin.

In some embodiments, the present invention provides a method for treating dry eye disease in a subject, comprising topically administering to an eye of a subject with dry eye disease a therapeutically effective amount of an ophthalmic solution of the invention. In some embodiments, a method of the invention comprises topically administering to an eye of a subject with dry eye disease an ophthalmic solution of the invention four times a day (QID). In some embodiments, a method of the invention comprises topically administering to an eye of a subject with dry eye disease an ophthalmic solution of the invention three times a day (TID). In some embodiments, a method of the invention comprises topically administering to an eye of a subject with dry eve disease an ophthalmic solution of the invention two times a day (BID) or once a day. In some embodiments, a method of the invention comprises topically administering to an eye of a subject with dry eye disease ophthalmic solution of the invention as needed (PRN).

In some embodiments, a method of the invention comprises topically administering an ophthalmic solution of the invention four times a day (QID) at initiation phase, followed by a maintenance phase wherein an ophthalmic solution of the invention is administered fewer than four times a day, for example, one, two, or three times a day.

BRIEF DESCRIPTION OF IRE DRAWINGS

DETAILED DESCRIPTION

Figure 1:
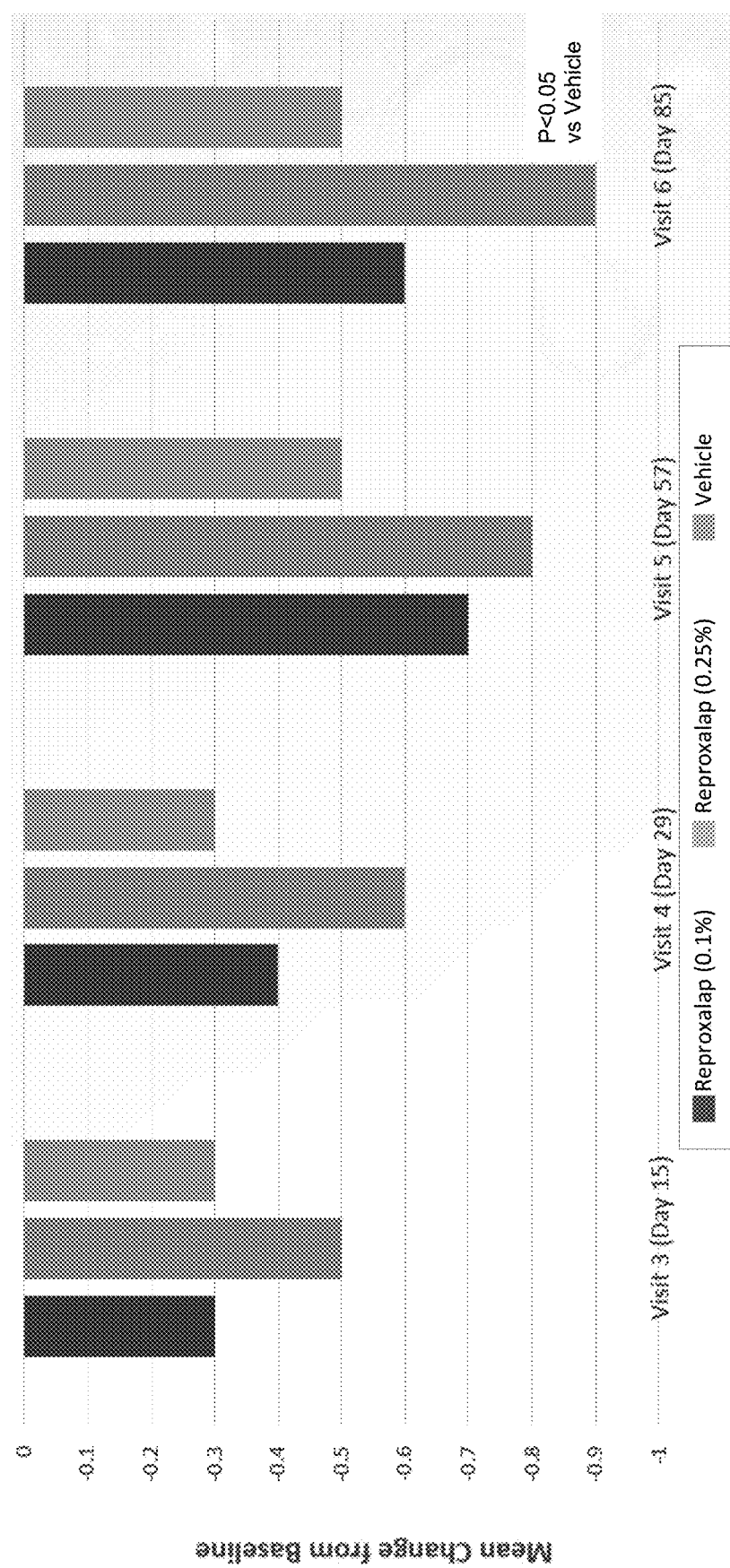
FIG. 1 depicts OD & 4-Symptom Questionnaire: Dryness (ITT Population with Observed Data Only).

1. General Description of Certain Embodiments of the Invention

Reproxalap topical ocular solution is being developed for treatment of ocular inflammation. The drug product, in various strengths, has completed a Phase 1 clinical trial, as well as a controlled, double-masked Phase 2a clinical trial in allergic conjunctivitis; a controlled, double-masked Phase 2b clinical trial in allergic conjunctivitis; a controlled, double-masked Phase 2 clinical trial in noninfectious anterior uveitis; a Phase 2a clinical trial in dry eye disease; and a controlled, double-masked Phase 2b clinical trial in dry eye disease. The maximum exposure to reproxalap in these completed clinical trials has been dosing with 0.5% w/v reproxalap for six weeks, for treating subjects with noninfectious anterior uveitis.

The objective of the Phase 2a clinical trial in dry eye disease was to assess the safety, tolerability, and pharmacodynamic activity of Reproxalap Ophthalmic Solutions in subjects with dry eye disease (DED) for 28 days of QID dosing with one of three different formulations. The formulations used were 0.1% w/v Reproxalap Ophthalmic Solution, and 0.5% w/v Reproxalap Ophthalmic Solution, and 0.5% w/v Ophthalmic Lipid Solution. No serious adverse events (SAEs) were observed during the 28-day treatment with any of the three reproxalap formulations, and no clinically significant change in visual acuity (VA), intraocular pressure (IOP), slit lamp biomicroscopic findings, or undilated funduscopic findings were observed. Drop comfort was less well tolerated with the 0.5% w/v Reproxalap Ophthalmic Solution and Ophthalmic Lipid Solution than with the 0.1% w/v Reproxalap Ophthalmic Solution. Statistically significant efficacy in within-subject improvement was observed over a broad array of DED signs and symptoms assessed as exploratory pharmacodynamics endpoints.

In a Phase 2b clinical trial, the efficacy of Reproxalap Ophthalmic Solutions (0.25% and 0.1%) were evaluated in patients with dry eye disease (see the details in Example 1). Administration of Reproxalap Ophthalmic Solutions for 12 weeks resulted in statistically significant improvements in multiple signs and symptoms. The efficacy profile of Reproxalap Ophthalmic Solutions was evident as early as two weeks following treatment initiation. Reproxalap Ophthalmic Solutions showed broad activity across signs, including tear quantity (Schirmer's Test), tear quality (Tear Film Breakup Time (TBUT) and tear osmolarity), and ocular surface staining. In addition, a dose response between 0.1% and 0.25% reproxalap dose strengths was demonstrated in the Phase 2b clinical trial. Reproxalap Ophthalmic Solutions were found to be safe and well tolerated in the 12-week study, with only mild-to-moderate adverse events, including transient ocular stinging upon instillation.

Accordingly, in some embodiments, the present invention provides an ophthalmic solution comprising reproxalap, or a pharmaceutically acceptable salt thereof, and a pharmaceutically acceptable excipient, wherein the concentration of reproxalap, or a pharmaceutically acceptable salt thereof, is about 0.5% wv or less and 0.1% w/v or greater. In some embodiments, the present invention provides a method for treating dry eye disease in a subject, comprising topically administering to an eye of a subject with dry eye disease an ophthalmic solution described.

2. Definitions

The general terms used herein are defined with the following meanings, unless explicitly stated otherwise.

The term "comprising" and "including" are used herein in their open-ended and non-limiting sense unless otherwise noted. It is to be further understood that where descriptions of various embodiments use the term "comprising" or "including," those skilled in the art would understand that in some specific instances, an embodiment can be alternatively described using language "consisting essentially of" or "consisting of."

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "pharmaceutically acceptable" is defined herein to refer to those compounds, biologic agents, materials, compositions and/or dosage forms, which are, within the scope of sound medical judgment, suitable for contact with the tissues a subject e.g., a mammal or human, without excessive toxicity, irritation allergic response and other problem complications commensurate with a reasonable benefit/risk ratio.

The term "treating" or "treatment" as used herein comprises a treatment relieving, reducing or alleviating at least one symptom in a subject or affecting a delay of progression of a disease, condition and/or disorder. For example, treatment can be the diminishment of one or several signs or symptoms of a disorder or complete eradication of a disorder. Within the meaning of the present invention, the term "treat" also denotes to arrest, delay the onset (e.g., the period prior to clinical manifestation of a disease) and/or reduce the risk of developing or worsening a disease.

The term "subject" or "patient" as used herein includes animals, such as mammals, e.g., humans, dogs, cows, horses, pigs, sheep, goats, cats, mice, rabbits, rats and transgenic non-human animals. In some embodiments, the subject is a human.

The term "about" or "approximately" shall have the meaning of within 10% of a given value or range. In some embodiments, the term "about" refers to within 10%, 9%, 8%, 7%, 6%, 5%, 4%, 3%, 2%, or 1% of a given value.

The term "w/v" as used herein refers to "gram/mL" (weight over volume), which is a concentration unit. For example, 7% w/v is equivalent to 70 mg/mL.

Reproxalap is of formula

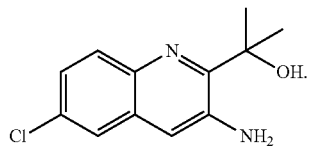 [SMILES: CC(C)(O)c1nc2ccc(Cl)cc2cc1N]

Without wishing to be bound by any particular theory, reproxalap functions as an aldehyde sequestering agent, or "trap", which binds rapidly to aldehydes and forms a cyclic product.

3. Ophthalmic Solutions

An ophthalmic solution of the invention comprises reproxalap, or a pharmaceutically acceptable salt thereof, at a concentration suitable for effectively treating dry eye disease, in particular without causing severe or intolerable adverse effects. In some embodiments, the present invention provides an ophthalmic solution comprising about 0.1% to 0.5% w/v reproxalap, or a pharmaceutically acceptable salt thereof, and a pharmaceutically acceptable excipient. In some embodiments, the excipient comprises a cyclodextrin, such as sulfobutylether β-cyclodextrin (SBECD) or hydroxypropyl β-cyclodextrin.

In some embodiments, an ophthalmic solution comprises repoxalap and a cyclodextrin excipient in a ratio of less than 1:2.1 on a mole:mole basis. In some embodiments, the ratio of reproxalap and cyclodextrin is about 1:2.1 to about 1:25 ratio on a mole:mole basis. In some embodiments, the ratio is about 1:2.2 to 1:20, 1:2.5 to 1:20, 1:2.5 to 1:10, 1:2.75 to 1:10, 1:3 to 1:8, 1:3.5 to 1:7, 1:4 to 1:6, or 1:4 to 1:5 in a mole:mole basis. In some embodiments, the ratio is about 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4.0, 1:4.1, 1:4.2, 1:4.3, 1:4.4, 1:4.5, 1:4.6, 1:4.7, 1:4.8, 1:4.9, 1:5.0, 1:5.1, 1:5.2, 1:5.3, 1:5.4, 1:5.5, 1:6, 1:7, 1:8, 1:9, 1:10, 1:12, 1:15, 1:20, or 1:25 on a mole:mole basis.

In some embodiments, the cyclodextrin excipient is one of those described herein, such as sulfobutylether β-cyclodextrin (SBECD). The average degree of substitution of the SBECD is about 6.5.

In some embodiments, the ratio of reproxalap to the excipient is about 1:2.1 or less on a mole:mole basis.

In some embodiments, the excipient is a cyclodextrin and the ratio of reproxalap to the excipient is about 1:2.1 to about 1:25 on a mole:mole basis.

In some embodiments, the excipient is a cyclodextrin and the ratio of reproxalap to the excipient is about 1:2 to about 1:5 on a mole:mole basis.

In some embodiments, the present invention provides an ophthalmic solution comprising reproxalap, or a pharmaceutically acceptable salt thereof, and a pharmaceutically acceptable excipient, wherein the concentration of reproxalap, or a pharmaceutically acceptable salt thereof, is about 0.5% w/v or less and about 0.1% w/v or greater. In some embodiments, the ophthalmic solution comprises about 0.15 to about 0.45% w/v reproxalap, or a pharmaceutically acceptable salt thereof, and a pharmaceutically acceptable excipient. In some embodiments, the ophthalmic solution comprises about 0.2 to about 0.4% w/v reproxalap, or a pharmaceutically acceptable salt thereof, and a pharmaceutically acceptable excipient. In some embodiments, the ophthalmic solution comprises about 0.21 to about 0.35% w/v reproxalap, or a pharmaceutically acceptable salt thereof, and a pharmaceutically acceptable excipient. In some embodiments, the ophthalmic solution comprises about 0.22 to about 0.3% w/v reproxalap, or a pharmaceutically acceptable salt thereof, and a pharmaceutically acceptable excipient. In some embodiments, the ophthalmic solution comprises about 0.22 to about 0.29% w/v reproxalap, or a pharmaceutically acceptable salt thereof, and a pharmaceutically acceptable excipient. In some embodiments, the ophthalmic solution comprises about 0.25% w/v reproxalap, or a pharmaceutically acceptable salt thereof, and a pharmaceutically acceptable excipient. In some embodiments, the ophthalmic solution comprises about 0.25% w/v reproxalap and a pharmaceutically acceptable excipient selected from a cyclodextrin. In some embodiments, the ophthalmic solution comprises about 0.5% w/v reproxalap and a pharmaceutically acceptable excipient selected from a cyclodextrin.

In some embodiments, the present invention provides an ophthalmic solution comprising less than 0.5% w/v reproxalap, or a pharmaceutically acceptable salt thereof, and a pharmaceutically acceptable excipient. In some embodiments, the present invention provides an ophthalmic solution comprising at least 0.1% w/v reproxalap, or a pharmaceutically acceptable salt thereof, and a pharmaceutically acceptable excipient. In some embodiments, the present invention provides an ophthalmic solution comprising reproxalap, or a pharmaceutically acceptable salt thereof, and a pharmaceutically acceptable excipient, wherein the concentration of reproxalap, or a pharmaceutically acceptable salt thereof, is less than 0.5% wv and 0.1% wv or greater.

In some embodiments, reproxalap, or a pharmaceutically acceptable salt thereof, in an ophthalmic solution of the invention is at a concentration of less than 0.45% w/v and at least 0.1% w/v. In some embodiments, reproxalap, or a pharmaceutically acceptable salt thereof, in an ophthalmic solution of the invention is at a concentration of less than 0.4% w/v and at least 0.1% w/v. In some embodiments, reproxalap, or a pharmaceutically acceptable salt thereof, in an ophthalmic solution of the invention is at a concentration of less than 0.35% w/v and at least 0.1% w/v. In some embodiments, reproxalap, or a pharmaceutically acceptable salt thereof, in an ophthalmic solution of the invention is at a concentration of less than 0.3% w/v and at least 0.1% w/v. In some embodiments, reproxalap, or a pharmaceutically acceptable salt thereof, in an ophthalmic solution of the invention is at a concentration of less than 0.25% w/v and more than 0.1% w/v. In some embodiments, reproxalap, or a pharmaceutically acceptable salt thereof, in an ophthalmic solution of the invention is at a concentration of less than 0.2% w/v and at least 0.1% w/v. In some embodiments, reproxalap, or a pharmaceutically acceptable salt thereof, in an ophthalmic solution of the invention is at a concentration of less than 0.15% w/v and at least 0.1% w/v.

In some embodiments, reproxalap, or a pharmaceutically acceptable salt thereof, in an ophthalmic solution of the invention is at a concentration of 0.5% w/v or less and at least 0.15% w/v. In some embodiments, reproxalap, or a pharmaceutically acceptable salt thereof, in an ophthalmic solution of the invention is at a concentration of 0.5% w/v or less and at least 0.2% w/v. In some embodiments, reproxalap, or a pharmaceutically acceptable salt thereof, in an ophthalmic solution of the invention is at a concentration of 0.5% w/v or less and at least 0.25% w/v. In some embodiments, reproxalap, or a pharmaceutically acceptable salt thereof, in an ophthalmic solution of the invention is at a concentration of 0.5% w/v or less and at least 0.3% w/v. In some embodiments, reproxalap, or a pharmaceutically acceptable salt thereof, in an ophthalmic solution of the invention is at a concentration of 0.5% w/v or less and at least 0.35% w/v. In some embodiments, reproxalap, or a pharmaceutically acceptable salt thereof, in an ophthalmic solution of the invention is at a concentration of 0.5% w/v or less and at least 0.4% w/v. In some embodiments, reproxalap, or a pharmaceutically acceptable salt thereof, in an ophthalmic solution of the invention is at a concentration of 0.5% w/v or less and at least 0.45% w/v.

In some embodiments, reproxalap, or a pharmaceutically acceptable salt thereof, in an ophthalmic solution of the invention is at a concentration of about 0.1% to 0.5%, 0.15% to 0.45% w/v, 0.15% to 0.4% w/v, 0.15% to 0.35% w/v, 0.15% to 0.3% w/v, 0.15% to 0.25% w/v, or 0.15% to 0.2% w/v. In some embodiments, reproxalap, or a pharmaceutically acceptable salt thereof, in an ophthalmic solution of the invention is at a concentration of 0.2% to 0.45% w/v, 0.2% to 0.4% w/v, 0.2% to 0.35% w/v, 0.2% to 0.3% w/v, or 0.2% to 0.25% w/v. In some embodiments, reproxalap, or a pharmaceutically acceptable salt thereof, in an ophthalmic solution of the invention is at a concentration of 0.25% to 0.45% w/v, 0.25% to 0.4% w/v, 0.25% to 0.35% w/v, or 0.25% to 0.3% w/v. In some embodiments, reproxalap, or a pharmaceutically acceptable salt thereof, in an ophthalmic solution of the invention is at a concentration of 0.3% to 0.45% w/v or 0.3% to 0.4% w/v.

In some embodiments, reproxalap, or a pharmaceutically acceptable salt thereof, in an ophthalmic solution of the invention is at a concentration of about 0.1% w/v, 0.15% w/v, about 0.2% w/v, about 0.25%, about 0.3% w/v, about 0.35% w/v, about 0.4% w/v, about 0.45% w/v or about 0.5% w/v.

In some embodiments, as further described herein, the foregoing concentrations of reproxalap can be selected and applied to treatment regimen that includes an initiation phase, an exacerbation phase, and/or a maintenance phase.

In some embodiments, a pharmaceutically acceptable excipient in an ophthalmic solution of the invention is a cyclodextrin. In some embodiments, a cyclodextrin is α-, β- and γ-cyclodextrin. In some embodiments, a cyclodextrin is a pharmaceutically acceptable derivative of a cyclodextrin, including, but not limited to, the hydroxyalkyl derivatives of β- and γ-cyclodextrin (especially the hydroxyethyl and hydroxypropyl derivatives of β-cyclodextrin and γ-cyclodextrin), randomly methylated β-cyclodextrin, sulfobutylether β-cyclodextrin, sulfobutylether γ-cyclodextrin, and the so-called branched β- and γ-cyclodextrin derivatives such as glucosyl-β-cyclodextrin and glucosyl-γ-cyclodextrin. The natural cyclodextrins are either used alone or in a mixture of two or more cyclodextrins, by way of non-limiting example, a mixture of the γ-cyclodextrin and the more water-soluble hydroxypropyl γ-cyclodextrin, or γ-cyclodextrin and sulfobutylether γ-cyclodextrin, or β-cyclodextrin and hydroxypropyl-β-cyclodextrin, or β-cyclodextrin and sulfobutylether β-cyclodextrin.

In some embodiments, a cyclodextrin in an ophthalmic solution of the invention is at a concentration of 0 to 20% w/v. In some embodiments, a cyclodextrin in an ophthalmic solution of the invention is at a concentration of 1 to 18% w/v, 1 to 16% w/v, 1 to 14% w/v, 2 to 12% w/v, 4 to 10% w/v, 5 to 9% w/v, or 6 to 8% w/v. In some embodiments, the cyclodextrin in an ophthalmic solution of the invention is at a concentration of 7% to 11% w/v. In some embodiments, a cyclodextrin in an ophthalmic solution of the invention is at a concentration of about 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 16% w/v, 17% w/v, 18% w/v, 19% w/v, or 20% w/v.

In some embodiments, a pharmaceutically acceptable excipient in an ophthalmic solution of the invention is sulfobutylether-β-cyclodextrin, in particular at any of the specified concentrations and ranges of concentrations above, such as about 7% w/v. In some embodiments, a pharmaceutically acceptable excipient in an ophthalmic solution of the invention is hydroxypropyl-β-cyclodextrin, in particular at any of the specified concentrations and ranges of concentrations specified above, such as about 7% w/v.

In some embodiments, the ophthalmic solution comprises about 0.2% to 0.4% w/v reproxalap and about 7% to 25% w/v of a cyclodextrin excipient such as SBECD. In some embodiments, the ophthalmic solution comprises about 0.2%, 0.25%, 0.3%, 0.35%, or 0.4% w/v reproxalap and about 7% to 25% w/v of a cyclodextrin excipient such as SBECD.

In some embodiments, the ophthalmic solution comprises about 0.25% w/v reproxalap and about 4.7 to about 25% w/v of a cyclodextrin excipient such as SBECD.

In some embodiments, the ophthalmic solution comprises about 0.25% w/v reproxalap and about 7% to 25% w/v of a cyclodextrin excipient such as SBECD.

In some embodiments, the ophthalmic solution comprises about 0.25% w/v reproxalap and about 4.75% to about 11% w/v of a cyclodextrin excipient such as SBECD.

In some embodiments, the ophthalmic solution comprises about 0.5% w/v reproxalap and about 9.5% to about 11% w/v of a cyclodextrin excipient such as SBECD. In some embodiments, the ratio of API to SBECD is about a mole of API per 2 moles of SBECD.

In some embodiments, the ophthalmic solution comprises about 0.25% w/v reproxalap and about 7% w/v of a cyclodextrin excipient such as SBECD. In some embodiments, the ratio of API to SBECD is about a mole of API per 3 moles SBECD.

In some embodiments, the ophthalmic solution comprises about 0.25% w/v reproxalap and about 11% w/v of a cyclodextrin excipient such as SBECD. In some embodiments, the ratio of API to SBECD is about a mole of API per 5 moles SBECD.

In some embodiments, an ophthalmic solution of the invention comprises a pharmaceutically acceptable buffering agent. In some embodiments, a pharmaceutically acceptable buffering agent is a phosphate buffer, citrate buffer, tris buffer, histidine buffer or acetate buffer.

In some embodiments, a pharmaceutically acceptable buffering agent is sodium phosphate, dibasic. In some embodiments, a pharmaceutically acceptable buffering agent is sodium phosphate, monobasic. In some embodiments, a pharmaceutically acceptable buffering agent is a mixture of sodium phosphate, dibasic, and sodium phosphate, monobasic. In some embodiments, an ophthalmic solution of the invention comprises about 0.083% w/v sodium phosphate, dibasic, and about 0.017% w/v sodium phosphate, monobasic.

In some embodiments, the ophthalmic solution of the invention is at an approximately neutral pH. In some embodiments, an ophthalmic solution of the invention is at a pH of 6.5 to 8. In some embodiments, an ophthalmic solution of the invention is at a pH of 6.9 to 7.7. In some embodiments, an ophthalmic solution of the invention is at a pH of 7.1 to 7.5. In some embodiments, an ophthalmic solution of the invention is at a pH of about 7.3.

Pharmaceutically acceptable acids and/or bases may be used in the ophthalmic solution to adjust pH. In some embodiments, an ophthalmic solution of the invention comprises a pharmaceutically acceptable acid. In some embodiments, an ophthalmic solution of the invention comprises a pharmaceutically acceptable base. In some embodiments, an ophthalmic solution of the invention comprises a pharmaceutically acceptable acid and base. In some embodiments, a pharmaceutically acceptable acid is hydrochloric acid. In some embodiments, pharmaceutically acceptable base is sodium hydroxide.

In some embodiments, an ophthalmic solution of the invention comprises a tonicity agent. In some embodiments, a tonicity agent is selected from the group consisting of dextrose, potassium chloride, propylene glycol, and sodium chloride. In some embodiments, an ophthalmic solution of the invention comprises a tonicity agent at a concentration of less than about 0.5% w/v. In some embodiments, an ophthalmic solution of the invention comprises a tonicity agent at a concentration of about 0.45%, 0.4%, 0.35%, 0.3%, 0.25%, 0.2%, 0.15%, or 0.1% w/v. In some embodiments, a tonicity agent is sodium chloride.

In some embodiments, the ophthalmic solution comprises reproxalap at the specified concentrations, cyclodextrin, phosphate, and sodium chloride. In some embodiments. In some embodiments, the ophthalmic solution comprises reproxalap at the specified concentrations herein (e.g., 0.1% w/v, 0.25% w/v, 0.5% w/v, etc.), 5 to 9% w/v cyclodextrin (e.g., sulfobutylether-β-cyclodextrin or hydroxypropyl-β-cyclodextrin); 0.07% to 0.09% w/v sodium phosphate (dibasic), 0.015% to 0.19% w/v sodium phosphate (monobasic), and 0.2 to 0.3% w/v sodium chloride. In some embodiments, the ophthalmic solution comprises reproxalap at the specified concentrations herein (e.g., 0.1% w/v, 0.25% v/v, 0.5% w/v, etc.), about 7% w/v cyclodextrin (e.g., sulfobutylether-β cyclodextrin or hydroxypropyl-β-cyclodextrin); 0.07% to 0.09% w/v sodium phosphate (dibasic), 0.015% to 0.019% w/v sodium phosphate (monobasic), and 0.2 to 0.3% w/v sodium chloride. In some embodiments, the ophthalmic solution is adjusted to an appropriate pH with sodium hydroxide or HCL.

In some embodiments, the ophthalmic solution comprises the following (0.5% Reproxalap Ophthalmic Solution A):

| Component | Amount (% w/v) | Grade |
|---|---|---|
| ADX-102 (reproxalap) | 0.5% | GMP |
| Sulfobutylether-beta-cyclodextrin (SBECD) | 9.5% | USP |
| Sodium phosphate, dibasic, anhydrous | 0.083% | USP |
| Sodium phosphate, monobasic, monohydrate | 0.017% | USP |
| Sodium hydroxide or Hydrochloric acid | pH adjustment | USP/NF |
| Sterile Water for Injection (WFI) | Dilute to volume | USP |

In some embodiments, the ophthalmic solution comprises the following (0.5% Reproxalap Ophthalmic Solution B)

| Component | Amount (% w/v) | Grade |
|---|---|---|
| ADX-102 (reproxalap) | 0.5% | GMP |
| Sulfobutylether-beta-cyclodextrin (SBECD) | 9.5% | USP |
| Sodium hydroxide or Hydrochloric acid | pH adjustment | USP/NF |
| Sterile Water for Injection (WFI) | Dilute to volume | USP |

In some embodiments, the ophthalmic solution comprises the following (0.25% Reproxalap Ophthalmic Solution A)

| Component | Amount (% w/v) | Grade |
|---|---|---|
| ADX-102 (reproxalap) | 0.25% | GMP |
| Sulfobutylether-beta-cyclodextrin (SBECD) | 7.0% | USP |
| Sodium phosphate, dibasic, anhydrous | 0.083% | USP |
| Sodium phosphate, monobasic, monohydrate | 0.017% | USP |
| Sodium chloride | 0.24% | USP |
| Sodium chloride | Tonicity adjustment | USP |
| Sodium hydroxide or Hydrochloric acid | pH adjustment | USP/NF |
| Sterile Water for Injection (WFI) | Dilute to volume | USP |

In some embodiments, the ophthalmic solution comprises the following (0.25% Reproxalap Ophthalmic Solution B)

| Component | Amount (% w/v) | Grade |
|---|---|---|
| ADX-102 (reproxalap) | 0.25% | GMP |
| Sulfobutylether-beta-cyclodextrin (SBECD) | 7.0% | USP |
| Sodium chloride | Tonicity adjustment | USP |
| Sodium hydroxide or Hydrochloric acid | pH adjustment | USP/NF |
| Sterile Water for Injection (WFI) | Dilute to volume | USP |

It is to be understood that variations of the ophthalmic solutions within the scope of the disclosure may be prepared given the guidance provided herein.

4. Methods of Treatment

In one aspect, the present invention provides a method for treating dry eye disease in a subject, comprising topically administering to an eye of a subject in need thereof a therapeutically effective amount of an ophthalmic solution of the invention. In some embodiments, the concentration of reproxalap in the ophthalmic solution used in the method is as described above.

In some embodiments, an ophthalmic solution of the invention can be administered at different frequencies suitable for effectively treating dry eye disease, for example, without causing severe or intolerable adverse effects.

In some embodiments, an ophthalmic solution of the invention can be topically administered one to six times a day. In some embodiments, a method of the invention comprises topically administering an ophthalmic solution of the invention six times a day. In some embodiments, a method of the invention comprises topically administering an ophthalmic solution of the invention five times a day. In some embodiments, a method of the invention comprises topically administering an ophthalmic solution of the invention four times a day (QID). In some embodiments, a method of the invention comprises topically administering an ophthalmic solution of the invention three times a day (TID). In some embodiments, a method of the invention comprises topically administering an ophthalmic solution of the invention two times a day (BID). In some embodiments, a method of the invention comprises topically administering an ophthalmic solution of the invention once a day (QD). In some embodiments, a method of the invention comprises topically administering an ophthalmic solution of the invention as needed (PRN).

In some embodiments, a method of the invention comprises topically administering to an eye of a subject with dry eye disease a therapeutically effective amount of an ophthalmic solution of the invention six times a day, five times a day, four times a day (QID), three times a day (TID), two times a day (BID), once a day (QD), followed by administration as needed (PRN).

In some embodiments, a method of the invention comprises topically administering an ophthalmic solution of the invention at various strengths (for example, at different reproxalap concentrations and different administration frequencies, as described herein).

In some embodiments, a method of the invention comprises topically administering an ophthalmic solution comprising about 0.25% w/v reproxalap, or a pharmaceutically acceptable salt thereof, four times a day, three times a day, or two times a day.

In some embodiments, a method of the invention comprises topically administering an ophthalmic solution comprising about 0.30% w/v reproxalap, or a pharmaceutically acceptable salt thereof, four times a day, three times a day, or two times a day.

In some embodiments, a method of the invention comprises topically administering an ophthalmic solution comprising about 0.35% w/v reproxalap, or a pharmaceutically acceptable salt thereof, four times a day, three times a day, or two times a day.

In some embodiments, a method of the invention comprises topically administering an ophthalmic solution comprising about 0.4% w/v reproxalap, or a pharmaceutically acceptable salt thereof, four times a day, three times a day, or two times a day.

In some embodiments, a method of the invention comprises topically administering an ophthalmic solution comprising about 0.45% w/v reproxalap, or a pharmaceutically acceptable salt thereof, four times a day, three times a day, or two times a day.

In some embodiments, a method of the invention comprises topically administering an ophthalmic solution comprising about 0.5% w/v reproxalap, or a pharmaceutically acceptable salt thereof, four times a day, three times a day, or two times a day.

In some embodiments, a method of the invention comprises topically administering an ophthalmic solution comprising 0.3% to 0.4% w/v reproxalap, or a pharmaceutically acceptable salt thereof, four times a day, three times a day, or two times a day.

In some embodiments, a method of the invention comprises topically administering an ophthalmic solution comprising 0.2% to 0.3% w/v reproxalap, or a pharmaceutically acceptable salt thereof, four times a day, three times a day, or two times a day.

In some embodiments, a method of the invention comprises topically administering an ophthalmic solution comprising 0.2% to 0.4% w/v reproxalap, or a pharmaceutically acceptable salt thereof, four times a day, three times a day, or two times a day.

In some embodiments, a method of the invention comprises two or more phases, wherein an ophthalmic solution of the invention is topically administering at different strengths in different phases. In some embodiments, a method of the invention comprises an initiation phase and a maintenance phase, wherein the ophthalmic solution is topically administered at a higher strength in the initiation phase than in the maintenance phase. In some embodiments, a treatment cycle of a method of the invention comprising multiple phases, including an exacerbation phase during which signs and/or symptoms become worse.

In some embodiments, the method of the invention comprises two or more phases, wherein an ophthalmic solution of the invention is topically administering at different strengths in different phases. In some embodiments, a method of the invention comprises an initiation phase, wherein the ophthalmic solution is topically administered at a high strength in the initiation phase, at a low strength in the maintenance phase, and at a high strength during an exacerbation of disease signs and/or symptoms.

In some embodiments, an ophthalmic solution administered in an initiation phase comprises a higher concentration of reproxalap, or a pharmaceutically acceptable salt thereof, than an ophthalmic solution administered in a maintenance phase. In some embodiments, the ophthalmic solution administered in an initiation phase or an exacerbation phase and the ophthalmic solution administered in a maintenance phase, comprises reproxalap, or a pharmaceutically acceptable salt, at a concentration selected from the group consisting of about 0.5% w/v, 0.45% w/v, 0.4% w/v, 0.35% w/v, 0.3% w/v, 0.25% w/v, 0.2% w/v, 0.15% w/v, and 0.1% w/v.

In some embodiments, an ophthalmic solution of about 0.5% w/v reproxalap is administered in an initiation phase or exacerbation phase, and less than 0.5% w/v reproxalap administered in a maintenance phase. In some embodiments, an ophthalmic solution of about 0.4% w/v, 0.35% w/v, 0.3% w/v, 0.25% w/v, 0.2% w/v, 0.15% w/v or 0.1% w/v reproxalap is administered in the maintenance phase.

In some embodiments, an ophthalmic solution of about 0.5% w/v to about 0.4% reproxalap is administered in an initiation phase or exacerbation phase, and less than 0.4% w/v reproxalap administered in a maintenance phase. In some embodiments, an ophthalmic solution of about 0.35% w/v, 0.3% w/v, 0.25% w/v, 0.2% w/v, 0.15% w/v or 0.1% w/v reproxalap is administered in the maintenance phase.

In some embodiments, an ophthalmic solution of about 0.5% w/v to about 0.3% reproxalap is administered in an initiation phase or exacerbation phase, and less than 0.3% w/v reproxalap administered in a maintenance phase. In some embodiments, an ophthalmic solution of about 0.25% w/v, 0.2% w/v, 0.15% w/v or 0.1% w/v reproxalap is administered in the maintenance phase.

In some embodiments, an ophthalmic solution of about 0.4% w/v to about 0.3% reproxalap is administered in an initiation phase or exacerbation phase, and less than 0.3% w/v reproxalap administered in a maintenance phase. In some embodiments, an ophthalmic solution of about 0.25% w/v, 0.2% w/v, 0.15% w/v or 0.1% w/v reproxalap is administered in the maintenance phase.

In some embodiments, an ophthalmic solution of about 0.3% w/v to about 0.2% reproxalap 0.3%, 0.25%, or 02% w/v) is administered in an initiation phase or exacerbation phase, and 0.25% w/v or less reproxalap administered in a maintenance phase. In some embodiments, an ophthalmic solution of about 0.25% w/v, 0.2% w/v, 0.15% w/v or 0.1% w/v reproxalap is administered in the maintenance phase.

In some embodiments, an ophthalmic solution of the invention is topically administered more frequently per day in an initiation phase and an exacerbation phase than in a maintenance phase. In some embodiments, an ophthalmic solution of the invention is topically administered five times a day in an initiation phase, followed by four, three, two, or one times a day in a maintenance phase. In some embodiments, an ophthalmic solution of the invention is topically administering four times a day in an initiation phase or exacerbation phase, followed by three, two, or one times a day in a maintenance phase. In some embodiments, an ophthalmic solution of the invention is topically administering three times a day in an initiation phase or exacerbation phase, followed by two or one times a day in a maintenance phase. In some embodiments, an ophthalmic solution of the invention is topically administering two times a day in an initiation phase or exacerbation phase, followed by once daily in a maintenance phase.

In some embodiments, an ophthalmic solution administered in an initiation phase or exacerbation phase is at a higher reproxalap concentration and higher administration frequency than an ophthalmic solution administered in a maintenance phase.

In some embodiments, the present invention provides a method for treating dry eye disease in a subject, comprising topically administering to the subject an ophthalmic solution comprising about 0.4% w/v reproxalap, or a pharmaceutically acceptable salt thereof, and a pharmaceutically acceptable excipient, wherein the ophthalmic solution is administered at a higher strength in an initiation phase or exacerbation phase followed by a lower strength in a maintenance phase, wherein each of the initiation phase, exacerbation phase, and maintenance phase is as described herein.

In some embodiments, a multiple phase treatment cycle can include an initiation phase or exacerbation phase of up to 12 weeks with an ophthalmic solution comprising about 0.5%, 0.4% or 0.35% w/v (e.g., 0.5% to 0.35% w/v) reproxalap, or a pharmaceutically acceptable salt thereof, is up to 12 weeks, followed by a maintenance phase. In some embodiments, an ophthalmic solution comprising about 0.5%, 0.4% or 0.35% w/v (e.g., 0.5% to 0.35% w/v) reproxalap, or a pharmaceutically acceptable salt thereof, is administered four times a day in an initiation phase or exacerbation phase followed by three, two, or one times a day in the maintenance phase. In some embodiments, an ophthalmic solution comprising about 0.5%, 0.4% or 0.35% w/v (e.g., 0.5% to 0.35% w/v) reproxalap, or a pharmaceutically acceptable salt thereof, is administered three times a day in an initiation phase or exacerbation phase followed by two or one times a day in the maintenance phase.

In some embodiments, an ophthalmic solution comprising about 0.4%, 0.35% or 0.3% w/v (e.g., 0.4% to 0.3% w/v) reproxalap, or a pharmaceutically acceptable salt thereof, is administered four times a day in an initiation phase or exacerbation phase followed by three, two, or one times a day in the maintenance phase. In some embodiments, an ophthalmic solution comprising about 0.4%, 0.35% or 0.3% w/v (e.g., 0.4% to 0.3% w/v) reproxalap, or a pharmaceutically acceptable salt thereof, is administered three times a day in an initiation phase or exacerbation phase followed by two or one times a day in the maintenance phase.

In some embodiments, an ophthalmic solution comprising about 0.3%, 0.25% or 0.2% w/v (e.g., 0.3% to 0.2% w/v) reproxalap, or a pharmaceutically acceptable salt thereof, is administered four times a day in an initiation phase or exacerbation phase followed by three, two, or one times a day in the maintenance phase. In some embodiments, an ophthalmic solution comprising about 0.3%, 0.25% or 0.2% w/v (e.g., 0.3% to 0.2% w/v) reproxalap, or a pharmaceutically acceptable salt thereof, is administered three times a day in an initiation phase or exacerbation phase followed by two or one times a day in the maintenance phase.

In some embodiments, the present invention provides a method for treating dry eye disease in a subject, comprising topically administering to the subject an ophthalmic solution comprising 0.35% to 0.45% w/v reproxalap, or a pharmaceutically acceptable salt thereof, and a pharmaceutically acceptable excipient, wherein the ophthalmic solution is administered at a higher strength in an initiation phase or exacerbation phase followed by a lower strength in a maintenance phase, wherein each of the initiation phase, exacerbation phase and maintenance phase is as described herein. In some embodiments, a multiple phase treatment cycle of an ophthalmic solution comprising 0.35% to 0.45% w/v reproxalap, or a pharmaceutically acceptable salt thereof, is up to 12 weeks. In some embodiments, an ophthalmic solution comprising 0.35% to 0.45% w/v reproxalap, or a pharmaceutically acceptable salt thereof, is administered four times a day in an initiation phase or exacerbation phase followed by three, two, or one times a day in maintenance phase. In some embodiments, an ophthalmic solution comprising 0.35%-0.45% w/v reproxalap, or a pharmaceutically acceptable salt thereof, is administered three times a day in an initiation phase or exacerbation phase followed by two or one times a day in maintenance phase.

In some embodiments, an ophthalmic solution is administered QID for about 10 to 14 weeks, preferably about 12 weeks. In some embodiments, an ophthalmic solution is administration QID for about 2 to 6 weeks, preferably about 4 weeks followed by administration BID for about 6 to 10 weeks, preferably about 8 weeks. In some embodiments, the ophthalmic solution for the foregoing treatment regimen is 0.25% w/v reproxalap, or a pharmaceutically acceptable salt thereof, and about 7% w/v SBECD.

In some embodiments, an ophthalmic solution is administered QID for about 2 to 6 weeks, preferably about 4 weeks, followed by administration BID for about 6 to 10 weeks, preferably about 8 weeks. In some embodiments, the ophthalmic solution for the foregoing treatment regimen is 0.25% w/v reproxalap, or a pharmaceutically acceptable salt thereof, and about 11% w/v SBECD.

In some embodiments, the present invention provides a method for treating certain subjects with dry eye disease. In some embodiments, a subject with dry eye disease is 18 years or older. In some embodiments, a subject with dry eye disease has a history of dry eye for at least six months prior to receiving the treatment of the invention. In some embodiments, a subject with dry eye disease has a history of use or desire to use eye drops for dry eye symptoms within six months prior to receiving the treatment of the invention.

In some embodiments, the present invention provides a method for treating a subject with dry eye disease, in particular moderate-to-severe dry-eye disease, comprising identifying subjects satisfying one or more of the following criteria for at least one eye, prior to receiving the treatment of the invention (for example, a screening performed at about one and/or two weeks before receiving the treatment):
  having a Schirmer's Test score of ≤10 mm and ≥1 mm;
  having a tear film break-up time (TFBUT©)≤5 seconds;
  having a corneal fluorescein staining score of ≥2 in at least one region (e.g., inferior, superior, or central);
  having a sum corneal fluorescein staining score of ≥4 based on the sum of the inferior, superior, and central regions; and
  having a total Lissamine green conjunctival score of ≥2 based on the sum of the temporal and nasal regions.

In some embodiments, a subject with dry eye disease is not a female patient who is pregnant, nursing, or planning a pregnancy. In some embodiments, a subject with dry eye disease has not previously used reproxalap ophthalmic solution.

In some embodiments, the present invention provides a method for treating a subject with dry eye disease comprising a screening to exclude subjects having one or more of the following conditions for at least one eye, prior to receiving the treatment of the invention:

having any clinically significant slit lamp findings that may include active blepharitis, meibomian gland dysfunction (MGD), lid margin inflammation, or active ocular allergies that may require therapeutic treatment;

having an ongoing ocular infection (bacterial, viral, or fungal), or active ocular inflammation;

having previously had laser-assisted in situ keratomileusis (LASIK) surgery within the last 12 months;

having any planned ocular and/or lid surgeries over the study period or any ocular surgery within six months; and having a known allergy and/or sensitivity to an ophthalmic solution of the invention or its components.

As described herein, an ophthalmic solution of the invention can achieve an early onset of effect in subjects with dry eye disease. As used herein, an "early onset effect" refers to early efficacy (e.g., within 1 to 2 weeks of initiation of treatment—in initiation or exacerbation phase) in ameliorating symptoms of dry eye disease. In some embodiments, the "early onset effect" is for the same dose and frequency of administration in the initiation or exacerbation phase. Accordingly, in some embodiments, the present invention provides a method for treating a subject with dry eye disease comprising topically administering to the subject an ophthalmic solution of the invention, wherein the ophthalmic solution is administered at a dose strength which can achieve an early onset profile. In some embodiments, an early onset profile comprises early onset of effect for symptoms (e.g., ocular discomfort including dryness, itchiness, tearing, burning, stinging, grittiness, cloudy vision, sensitivity to environment, stringy ocular secretion). In some embodiments, an early onset profile comprises early onset of effect for signs (e.g., ocular vital staining, tear film break-up time, tear osmolarity, tear volume).

In some embodiments, a dose strength which can achieve an early onset of effect comprises topically administering an ophthalmic solution comprising reproxalap, or a pharmaceutically acceptable salt thereof, at a concentration as described herein. In some embodiments, a dose strength which can achieve an early onset of effect comprises topically administering an ophthalmic solution comprising reproxalap, or a pharmaceutically acceptable salt thereof, at a frequency at described herein. In some embodiments, a dose strength which can achieve an early onset of effect comprises topically administering an ophthalmic solution comprising reproxalap, or a pharmaceutically acceptable salt thereof, at a concentration and a frequency at described herein.

In some embodiments, a method of the invention can achieve an onset of effect in about two weeks. At different dose strengths (for example, different concentration and administering frequency), a method of the invention can achieve an onset in fewer than about two weeks. For example, in some embodiments, a method of the invention can achieve an onset in about 14, 13, 12, 11, ten, nine, or eight days. At a certain dose strength, a method of the invention can achieve an onset in about one week or less. In some embodiments, a method of the invention can achieve an onset in about seven, six, five, four, three, two, or one days.

In some embodiments, the present invention provides a method for treating dry eye disease in a subject, comprising topically administering to the subject an ophthalmic solution comprising about 0.5% w/v reproxalap, or a pharmaceutically acceptable salt thereof, and a pharmaceutically acceptable excipient, wherein the ophthalmic solution is administered three, two, or one times a day. In some embodiments, an ophthalmic solution comprising about 0.5% w/v reproxalap, or a pharmaceutically acceptable salt thereof, is administered three times a day. In some embodiments, an ophthalmic solution comprising about 0.5% w/v reproxalap, or a pharmaceutically acceptable salt thereof is administered two times a day. In some embodiments, an ophthalmic solution comprising about 0.5% w/v reproxalap, or a pharmaceutically acceptable salt thereof, is administered once daily.

In some embodiments, the present invention provides a method for treating dry eye disease in a subject, comprising topically administering to the subject an ophthalmic solution comprising about 0.5% w/v reproxalap, or a pharmaceutically acceptable salt thereof, and a pharmaceutically acceptable excipient, wherein the ophthalmic solution is administered at a higher strength in an initiation phase or exacerbation phase, followed by a lower strength in a maintenance phase, wherein each of the initiation phase, exacerbation phase, and maintenance phase is as described herein. In some embodiments, an ophthalmic solution comprising about 0.5% w/v reproxalap, or a pharmaceutically acceptable salt thereof is administered four times a day in an initiation phase or exacerbation phase followed by three, two, or one times a day in a maintenance phase. In some embodiments, an ophthalmic solution comprising about 0.5% w/v reproxalap, or a pharmaceutically acceptable salt thereof, is administered three times a day in an initiation phase or exacerbation phase followed by two or one times a day in a maintenance phase. In some embodiments, an ophthalmic solution comprising about 0.5% w/v reproxalap, or a pharmaceutically acceptable salt thereof, is administered two times a day in an initiation phase followed by one time a day in a maintenance phase. In some embodiments, an ophthalmic solution comprising about 0.5% w/v reproxalap, or a pharmaceutically acceptable salt thereof, is topically administered in an initiation phase or exacerbation phase, followed by topical administration of an ophthalmic solution comprising less than about 0.5% w/v reproxalap, or a pharmaceutically acceptable salt thereof, in a maintenance phase, wherein the administration frequency of each ophthalmic solution is selected from those as described above.

EXEMPLIFICATION

The following examples are intended to illustrate the invention and are not to be construed as being limitations thereon. Reproxalap can be synthesized as reported previously, for example, in WO 2006/127945, the entire content of which is incorporated herein by reference.

Abbreviations

CAE: controlled adverse environment
GMP: Good Manufacturing Practice
ICH: International Council for Harmonization of Technical Requirements for Pharmaceuticals for Human Use
OD: right eye
OS: left eye
OU: both eyes
PRN: as needed
QD: once daily
QID: Four times daily
QS: as much as will suffice Example 1

A Multi-Center, Phase 2b, Randomized, Double-Masked, Parallel-Group, Vehicle-Controlled, Clinical Study to Assess the Safety and Efficacy of Reproxalap Ophthalmic Solution (0.25% and 0.1%) Compared to Vehicle in Subjects with Dry Eye Disease Objectives:

To evaluate the efficacy of Reproxalap Ophthalmic Solutions (0.25% and 0.1%) on baseline to weeks 2, 4, 8, and 12 change scores for sign and symptom endpoints of dry eye disease.

To evaluate effect sizes for efficacy endpoints of Reproxalap Ophthalmic Solutions (0.25% and 0.1%) vs vehicle for the treatment of the signs and symptoms of dry eye disease to confirm the endpoint selection and sample size for Phase 3 studies.

To evaluate the safety and tolerability of Reproxalap Ophthalmic Solutions (0.25% and 0.1%) to vehicle for the treatment of the signs and symptoms of dry eye disease.

Investigational Product:
1) Reproxalap Ophthalmic Solution (0.25%)
2) Reproxalap Ophthalmic Solution (0.1%)
3) Vehicle Ophthalmic Solution In the Phase 2b study, reproxalap was formulated as an ophthalmic solution as described in the specification.

Duration: A subject's participation was estimated to be approximately 14 weeks (98 days).

Dosage/Dose Regimen/Instillation/Application/Use:
Screening: Between Visits 1 and 2, all subjects received 14 consecutive days (±2) of Run-in (vehicle) ocular drops self-administered QID in both eyes.

Treatment: During the 12-week (84±3 days) treatment period, Reproxalap Ophthalmic Solution at concentrations of 0.1%, 0.25%, or vehicle ophthalmic solution was administered QID by bilateral topical ocular dosing. Subjects were randomized to one of three treatment groups (1:1:1) to receive study drug after the Post-CAE® assessments at Visit 2.

Summary of Visit Schedule: Six visits over the course of approximately 14 weeks
 Visit 1=Day −14÷2. CAE® Screening
 Visit 2=Day 1, CAE® Confirmation/Baseline
 Visit 3=Day 15±2, 2-Week Follow-Up
 Visit 4=Day 29±2, 4-Week Follow-Up
 Visit 5=Day 57±3, 8-Week Follow-Up
 Visit 6=Day 85±3, 12-Week CAE® Follow-Up & Study Exit Condition/Disease: Dry Eye Disease (DED)

Inclusion Criteria: Subjects for treatment were based on the following criteria:
1 Been at least 18 years of age of either gender and any race;
2 Provide written informed consent and sign the Health Information Portability and Accountability Act (HIPAA) form;
3 Had a reported history of dry eye for at least six months prior to Visit 1;
4 Had a history of use or desire to use eye drops for dry eye symptoms within six months of Visit 1;
5 Reported a score of ≥2 on the Ora Calibra® Ocular Discomfort & 4-Symptom Questionnaire in at least one symptom at Visit 1 and Visit 2 Pre-CAE®;
6 Had a Schirmer's Test score of ≤10 mm and ≥1 mm at Visit 1 and Visit 2;
7 Had a tear film break-up time (TFBUT©) ≤5 seconds at Visit 1 and Visit 2 Pre-CAE®.
8 Had a corneal fluorescein staining score of ≥2 in at least one region (e.g., inferior, superior, or central) at Visit 1 and Visit 2 Pre-CAE®;
9 Have a sum corneal fluorescein staining score of ≥4, based on the sum of the inferior, superior, and central regions, at Visit 1 and Visit 2 Pre-CAE®;
10 Had a total Lissamine green conjunctival score of ≥2, based on the sum of the temporal and nasal regions at Visit 1 and Visit 2 Pre-CAE®;
11 Demonstrated a response to the CAE® at Visits 1 and 2 as defined by:
 A. Having at least a ≥1 point increase in fluorescein staining in the inferior region in at least one eye following CAE® exposure;
 B. Reporting an Ocular Discomfort score ≥3 at two or more consecutive time points in at least one eye during CAE® exposure (if a subject had an Ocular Discomfort rating of 3 at time=0 for an eye, s/he must have reported an Ocular Discomfort rating of 4 for two consecutive measurements for that eye). Note: a subject could not have an Ocular Discomfort score of 4 at time=0);
12 Had at least one eye, the same eye, satisfy all criteria for 6, 7, 8, 9, 10, and 11 above.

Exclusion Criteria: Subject were excluded based on the following criteria:
1 Had any clinically significant slit lamp findings at Visit 1 that may have included active blepharitis, meibomian gland dysfunction (MGD), lid margin inflammation, or active ocular allergies that require therapeutic treatment, and/or in the opinion of the investigator, might have interfered with study parameters;
2 Been diagnosed with an ongoing ocular infection (bacterial, viral, or fungal), or active ocular inflammation at Visit 1;
3 Worn contact lenses within seven days of Visit 1 or anticipate using contact lenses during the study;
4 Used any eye drops within 2 hours of Visit 1;
5 Had laser-assisted in situ keratomileusis (LASIK) surgery within the last 12 months;
6 Used cyclosporine 0.05% or lifitegrast 5.0% ophthalmic solution within 90 days of Visit 1;
7 Had any planned ocular and/or lid surgeries over the study period or any ocular surgery within 6 months of Visit 1;
8 Been using or anticipated using temporary punctal plugs during the study that had not been stable within 30 days of Visit 1;
9 Been currently taking any topical ophthalmic prescription (including medications for glaucoma) or over-the-counter (OTC) solutions, artificial tears, gels or scrubs, and cannot discontinue these medications for the duration of the trial (excluding medications allowed for the conduct of the study);
10 Had corrected visual acuity greater than or equal to logarithm of the minimum angle of resolution (logMAR)+0.7 as assessed by Early Treatment of Diabetic Retinopathy Study (ETDRS) scale in both eyes at Visit 1;
11 Been a woman who is pregnant, nursing, or planning a pregnancy;
12 Been unwilling to submit a urine pregnancy test at Visit 1 and Visit 6 (or early termination visit) if of childbearing potential. Non-childbearing potential was defined as a woman who is permanently sterilized (e.g., has had a hysterectomy or tubal ligation), or was postmenopausal (without menses for 12 consecutive months);
13 Been a man or woman of childbearing potential who was not using an acceptable means of birth control; acceptable methods of contraception include: hormonal—oral, implantable, injectable, or transdermal contraceptives; mechanical—spermicide in conjunction with a barrier such as a diaphragm or condom; intrauterine device (IUD); or surgical sterilization of partner. For non-sexually active males or females, abstinence may have been regarded as an adequate method of birth control; however, if the subject became sexually active during the study, he/she must have agreed to use adequate birth control as defined above for the remainder of the study;
14 Had a known allergy and/or sensitivity to the test article or its components;
15 Had a condition or be in a situation which the investigator feels may have put the subject at significant risk, confounded the study results, or interfered significantly with the subject's participation in the study;
16 Been currently enrolled in an investigational drug or device study or have used an investigational drug or device within 30 days of Visit 1;
17 Previously used reproxalap ophthalmic solution;
18 Been currently using any medication known to cause ocular drying that wass not used on a stable dosing regimen for at least 30 days prior to Visit 1;
19 Been unable or unwilling to follow instructions, including participation in all study assessments and visits.

The following efficacy measures and endpoints were used in the study:
Lissamine green staining (Ora Calibra® scale); regions: inferior, superior, central, temporal, nasal, corneal sum, conjunctival sum, and total eye score
Fluorescein staining (Ora Calibra® scale); regions: central, superior, inferior, temporal, nasal, corneal SUM, conjunctival sum, and total eye score)
Tear film break-up time
Unanesthetized Schirmer's Test
Ora Calibra® Ocular Discomfort Scale
Ora Calibra® Ocular Discomfort & 4-Symptom Questionnaire
Ocular Surface Disease Index (OSDI)©
SANDE questionnaire
Tear Osmolarity
Safety Measures:
Visual acuity
Slit-lamp evaluation
Adverse event query
Intraocular Pressure (IOP)
Dilated fundoscopy
General Statistical Methods and Types of Analyses
Sample Size: The study sample size of 100 per group was selected based on prior Phase 2 and 3 clinical trial results using the DED Hybrid CAE study design with other development programs and the effect size seen in Phase 2a with reproxalap on change from baseline after four weeks of treatment. This sample size wass deemed sufficient to assess the effect size on the DED sign and symptom endpoints with reproxalap vs vehicle, to confirm the endpoint selection and sample size needed for Phase 3 studies with reproxalap. A sample size of 100 per group provided 90% power at $\alpha=0.05$ to detect an effect size of 0.26 for inferior Lissamine green staining (Ora Calibra® scale), assuming a common standard deviation of 0.56 and an effect size of 0.44 for ocular discomfort assessed with the Ora Calibra® Ocular Discomfort Scale assuming a common standard deviation of 0.97.
Efficacy Analysis
Evaluated baseline to weeks 2, 4, 8 and 12 change scores with reproxalap on DED sign and symptom endpoints (both pre-CAE and CAE endpoints). Each endpoint was analyzed at a two-sided alpha level of 0.05, and the overall type I error was not controlled for in this investigative study.
Evaluated effect size of baseline to weeks 2, 4, 8 and 12 change scores of reproxalap vs vehicle on DED sign and symptom endpoints (both pre-CAE and CAE endpoints) to confirm the endpoint selection for primary outcome parameters and sample size for Phase 3 studies with reproxalap.
Sub-group analyses on effect size of baseline to weeks 2, 4, 8 and 12 change scores of reproxalap vs vehicle on DED sign and symptom endpoints (both pre-CAE and CAE endpoints) [Subgroups were prospectively detailed in the Statistical Analysis Plan (SAP)].

TABLE 1

Summary of Subject Disposition

|  | Reproxalap (0.1%) N = 100 | Reproxalap (0.25%) N = 100 | Vehicle N = 100 | All Subjects N = 300 |
|---|---|---|---|---|
| Intent-to-Treat Population | 100 (100.0%) | 100 (100.0%) | 100 (100.0%) | 300 (100.0%) |
| Per Protocol Population | 97 (97.0%) | 86 (86.0%) | 98 (98.0%) | 281 (93.7%) |
| Safety Population | 100 (100.0%) | 100 (100.0%) | 100 (100.0%) | 300 (100.0%) |
| Study Completion |  |  |  |  |
| Completed | 97 (97.0%) | 88 (88.0%) | 99 (99.0%) | 284 (94.7%) |
| Discontinued | 3 (3.0%) | 12 (12.0%) | 1 (1.0%) | 16 (5.3%) |
| Reason for Study Withdrawal |  |  |  |  |
| Adverse Events | 2 (2.0%) | 10 (10.0%) | 0 | 12 (4.0%) |
| Administrative Reasons | 1 (1.0%) | 0 | 0 | 1 (0.3%) |
| Withdrawal by Subject | 0 | 1 (1.0%) | 1 (1.0%) | 2 (0.7%) |
| Other | 0 | 1 (1.0%) | 0 | 1 (0.3%) |

TABLE 2

Phase 2b AE Summary

|  | Repruxalap 0.1% (N = 100) | Reproxalap 0.25% (N = 100) | Vehicle (N = 100) | All Subjects (N = 300) |
|---|---|---|---|---|
| Number of Ocular TEAEs | 47 | 111 | 15 | 173 |
| Number of Subjects with Ocular TEAEs | 38 (41.0%) | 93 (93.0%) | 13 (13.0%) | 144 (48.0%) |
| Mild | 37 (37.0%) | 84 (84.0%) | 12 (12.0%) | 133 (44.3%) |
| Moderate | 1 (1.0%) | 8 (8.0%) | 1 (1.0%) | 10 (3.3%) |
| Severe | 0 | 1 (10%) | 0 | 1 (0.3%) |
| Installation Site Pain Total | 37 (37.0%) | 93 (93.0%) | 2 (2.0%) | 132 (44.0%) |
| Prior to Day 15 | 31 (31.0%) | 89 (89.0%) | 1 (1.0%) | 121 (40.3%) |
| Day 15-Day 28 | 4 (4.0%) | 4 (4.0%) | 0 | 8 (2.7%) |
| Day 29-Day 56 | 2 (2.0%) |  | 1 (1.0%) | 3 (1.0%) |
| After Day 56 | 0 | 0 | 0 | 0 |
| Number of Subjects with TEAEs leading to Discontinuation | 1 | 10 |  |  |
| Prior to Day 15 | 1* | 7** |  |  |
| Day 15-Day 28 | 0 | 2*** | 0 | 11 (3.7%) |
| Day 29-Day 56 | 0 | 0 |  |  |
| After Day 56 | 0 | 1 (SAE) |  |  |

TABLE 2-continued

Phase 2b AE Summary

|  | Repruxalap 0.1% (N = 100) | Reproxalap 0.25% (N = 100) | Vehicle (N = 100) | All Subjects (N = 300) |
|---|---|---|---|---|
| Number of SAEs | 1 (peripheral vertigo, not related, stayed on study) | 1 (chest pain, not related) | 0 | 2 (0.7%) |

*Subject discontinued at Day 12
**Subjects discontinued on the following Days: 2, 3, 5, 5, 5, 12, 14
***Subjects discontinued on the following Days: 15, 16

Figure 2:
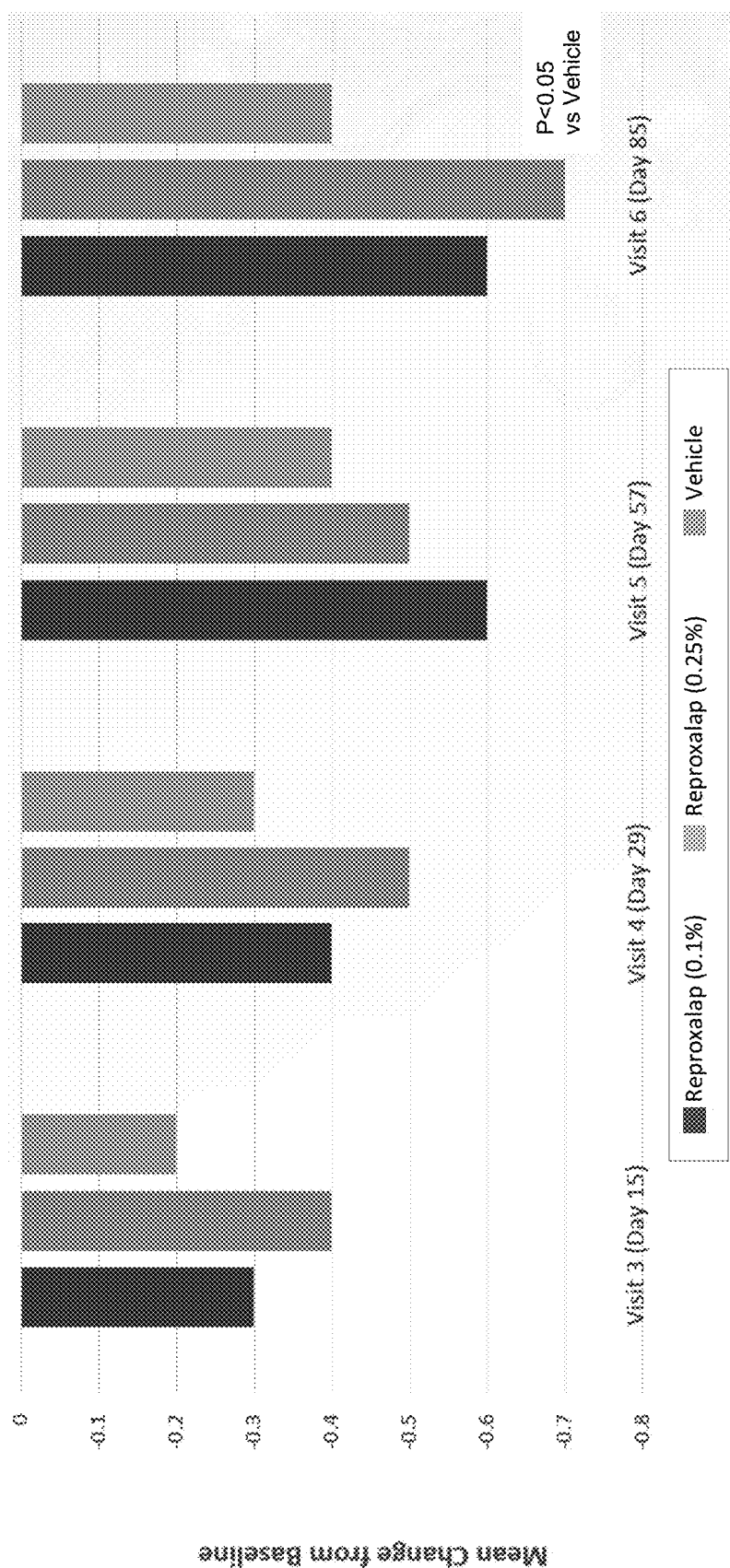
FIG. 2 depicts OD & 4-Symptom Questionnaire: Overall Ocular Discomfort (ITT Population with Observed Data Only).
Figure 3:
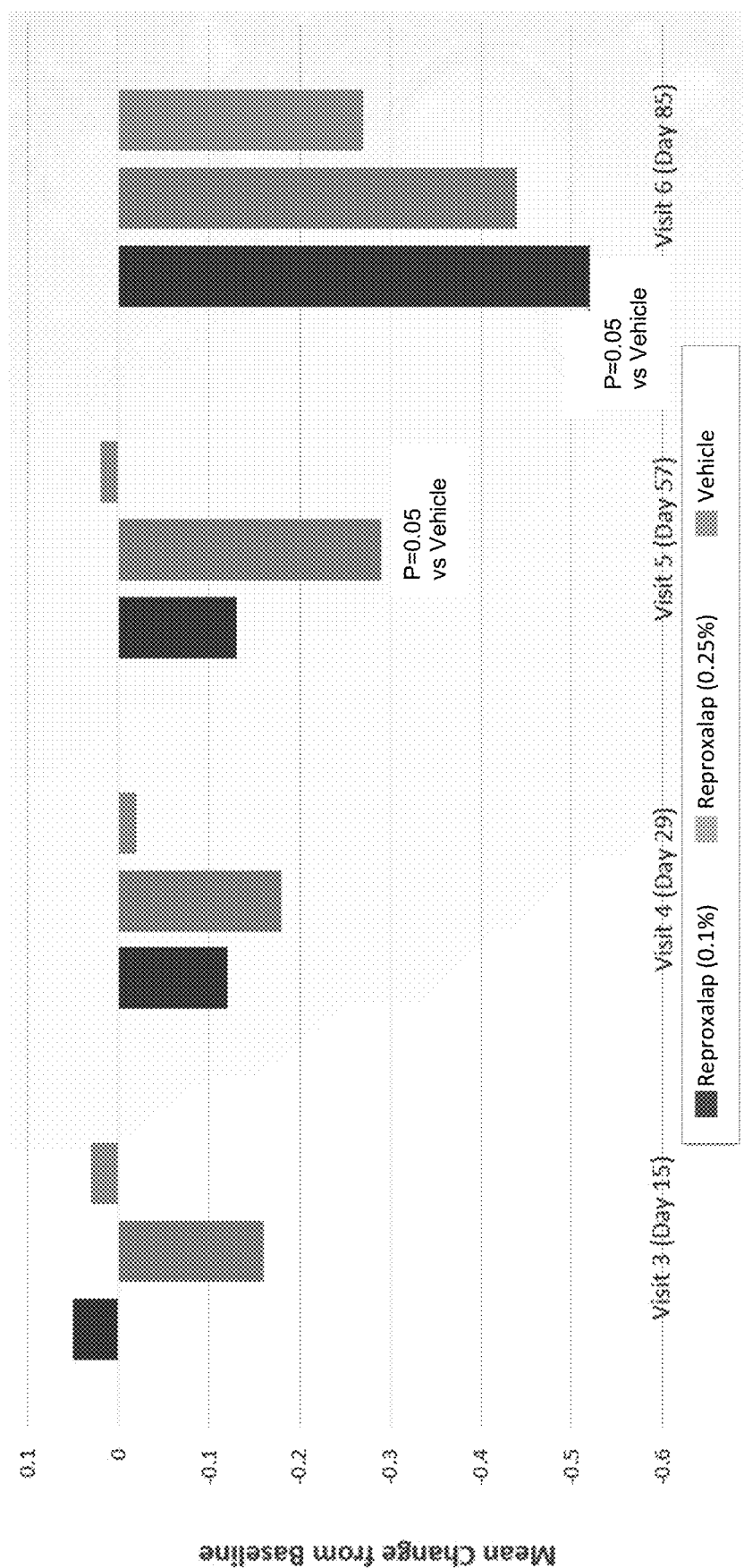
FIG. 3 depicts Fluorescein Staining: Conjunctival Sum Score (Nasal and Temporal) (ITT Population with Observed Data Only).
Figure 4:
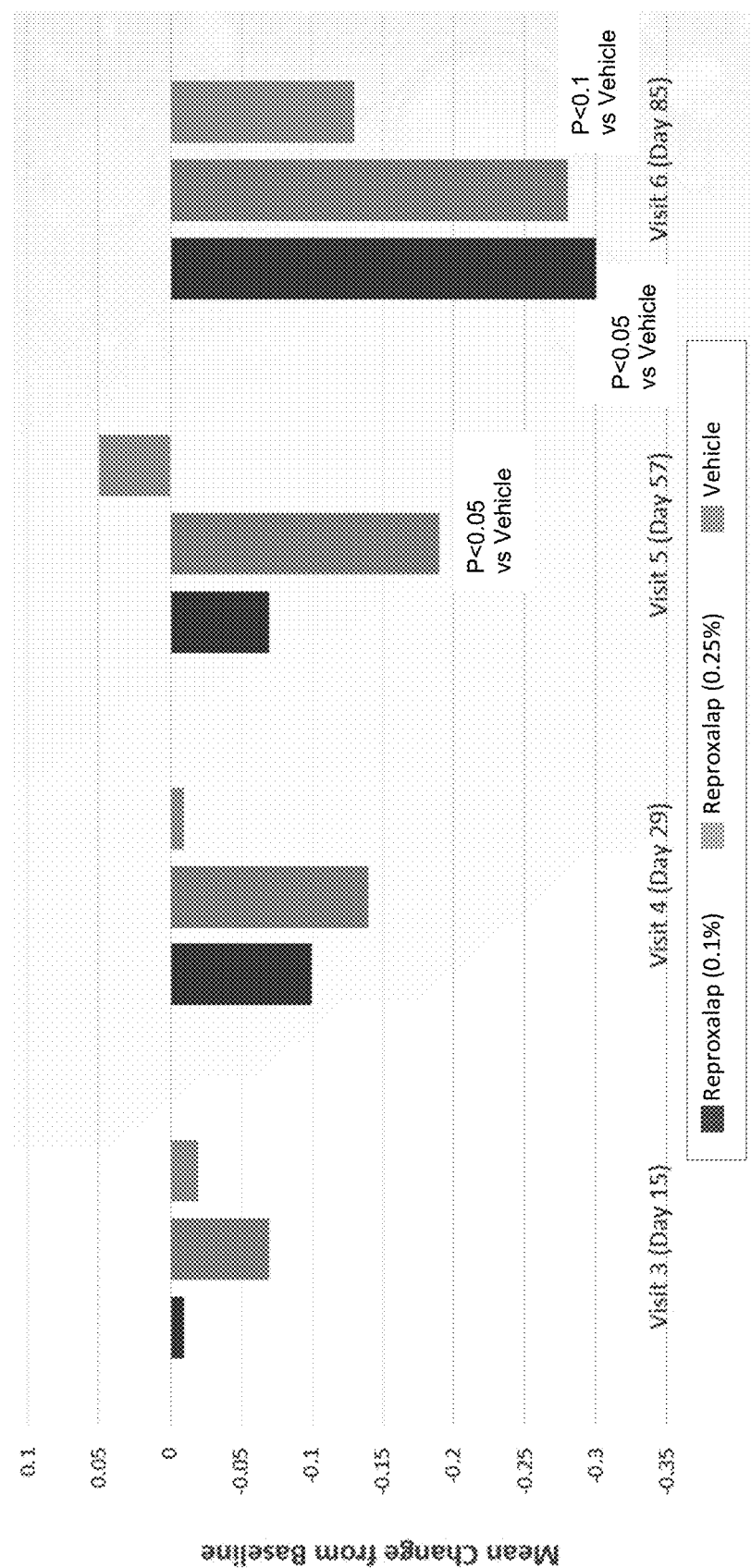
FIG. 4 depicts Fluorescein Staining: Nasal (ITT Population with Observed Data Only).
Figure 5:
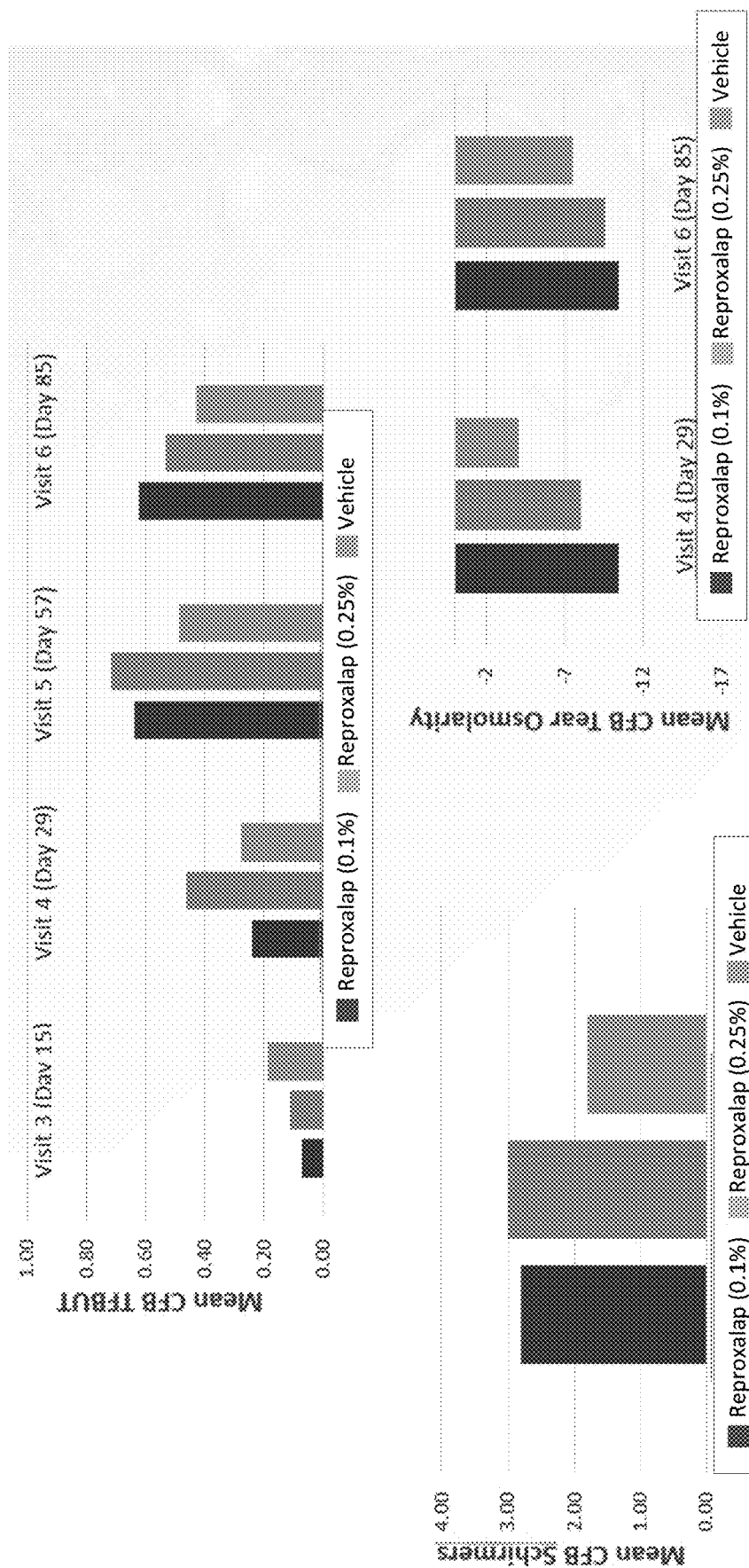
FIG. 5 depicts Tear Quantity and Quality Improved: Tear Film Break-Up Time, Schirmer's Test & Tear Osmolarity Supports Broad. Activity Profile (Endpoint Specific Worst Eye: ITT Population with Observed Data Only).
Figure 6:
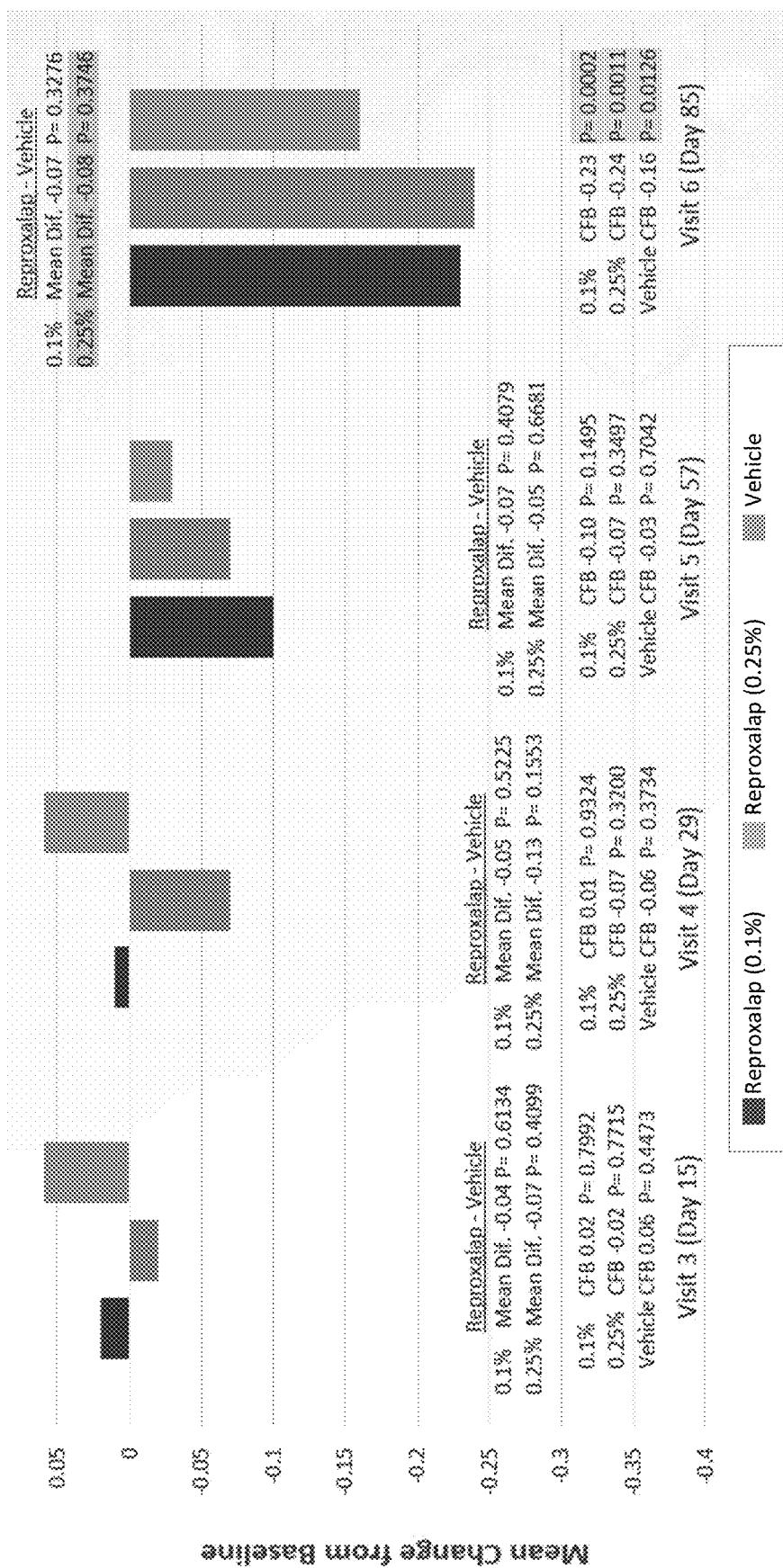
FIG. 6 depicts that CAE Endpoints are Confounded by Clear Efficacy at Week 12 Baseline Lissamine Green Staining: Inferior (ITT Population with Observed Data Only).
Figure 7:
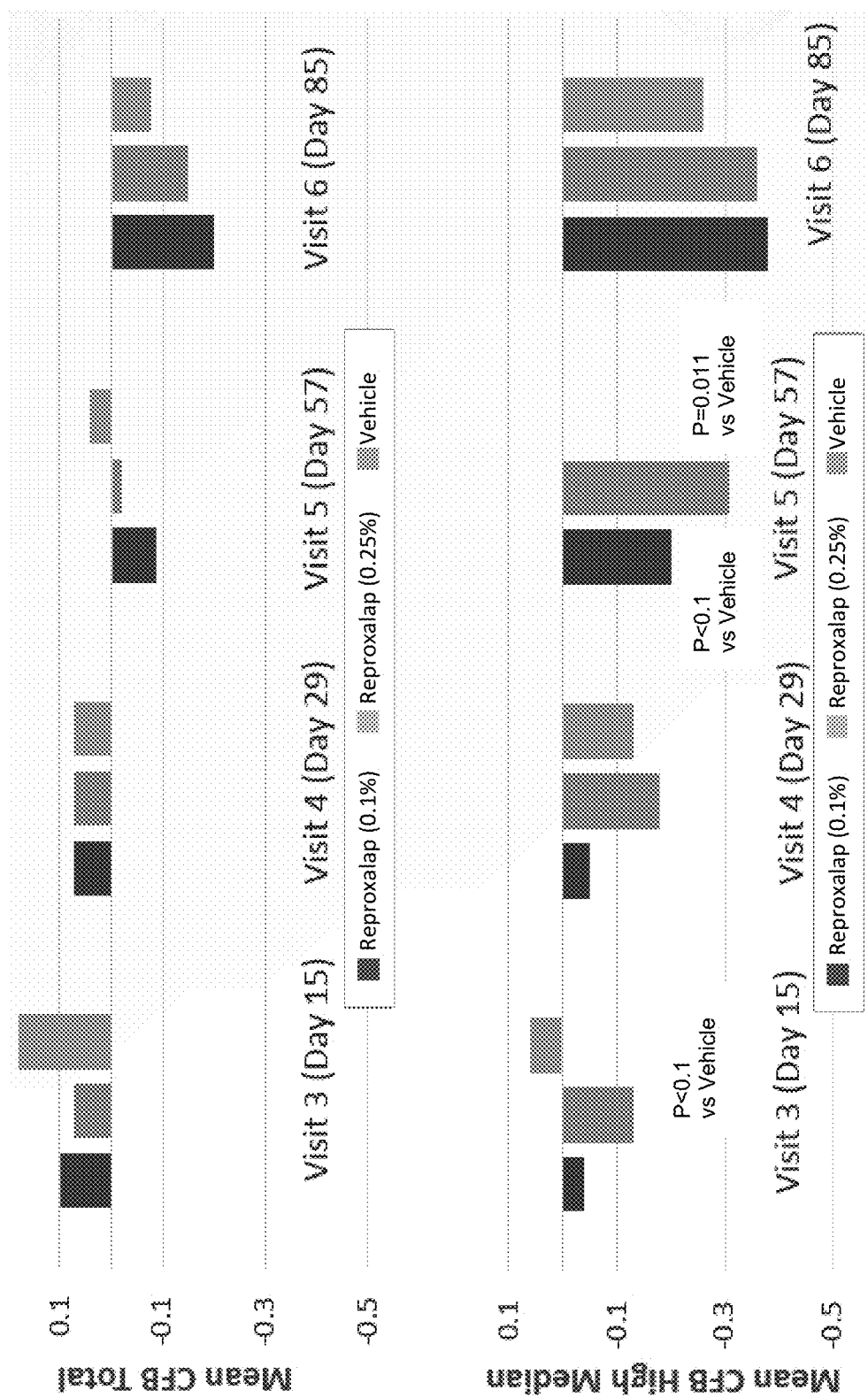
FIG. 7 depicts Fluorescein Staining: inferior Total Population (N=100/100/100) vs High Median Subgroup (N=68/69/66) (ITT Population with Observed Data Only).
Figure 8:
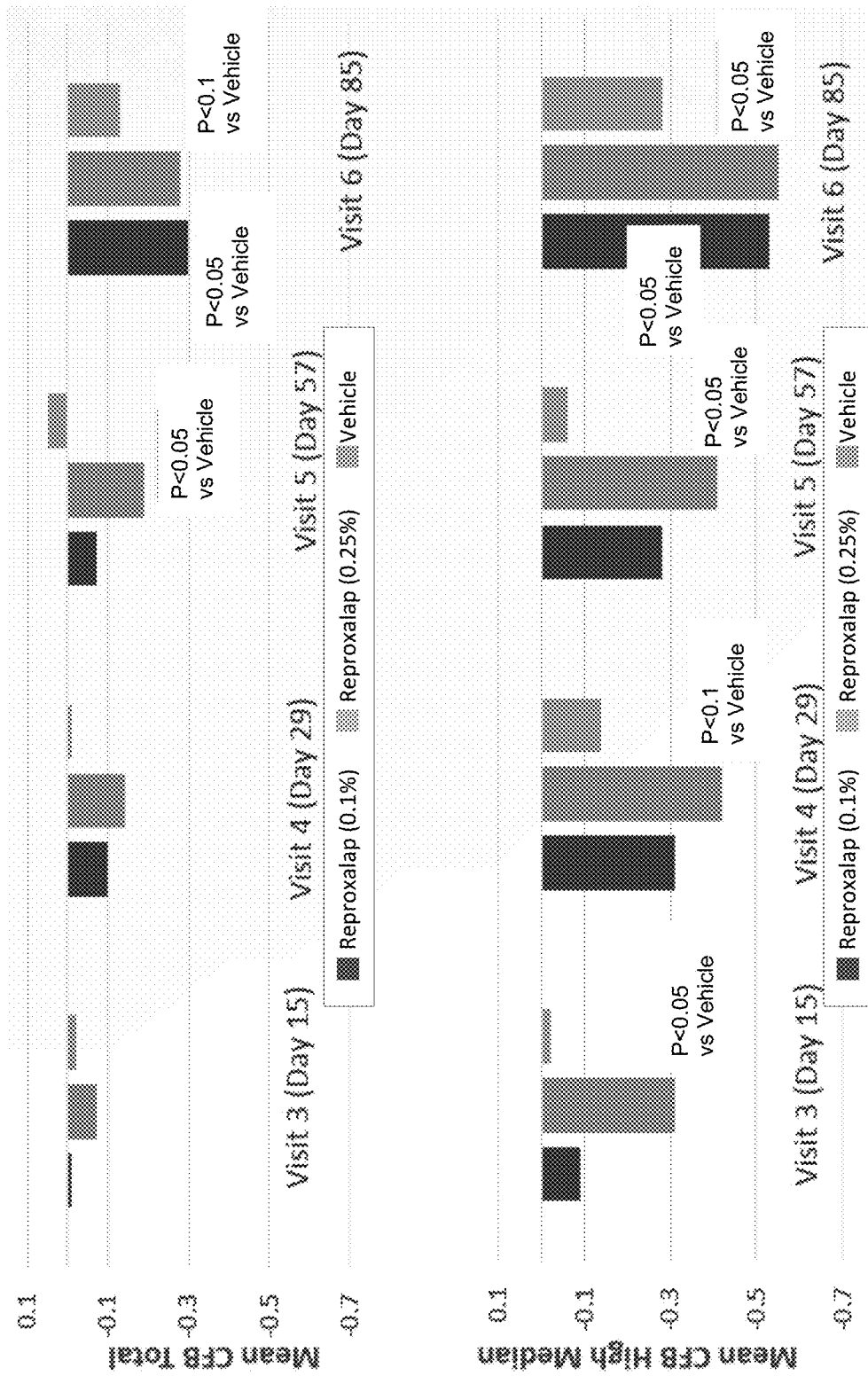
FIG. 8 depicts Fluorescein Staining: Nasal Total Population (N=100/100/100) vs High Median Subgroup (N=59/56/62) (ITT Population with Observed Data Only).
Figure 9:
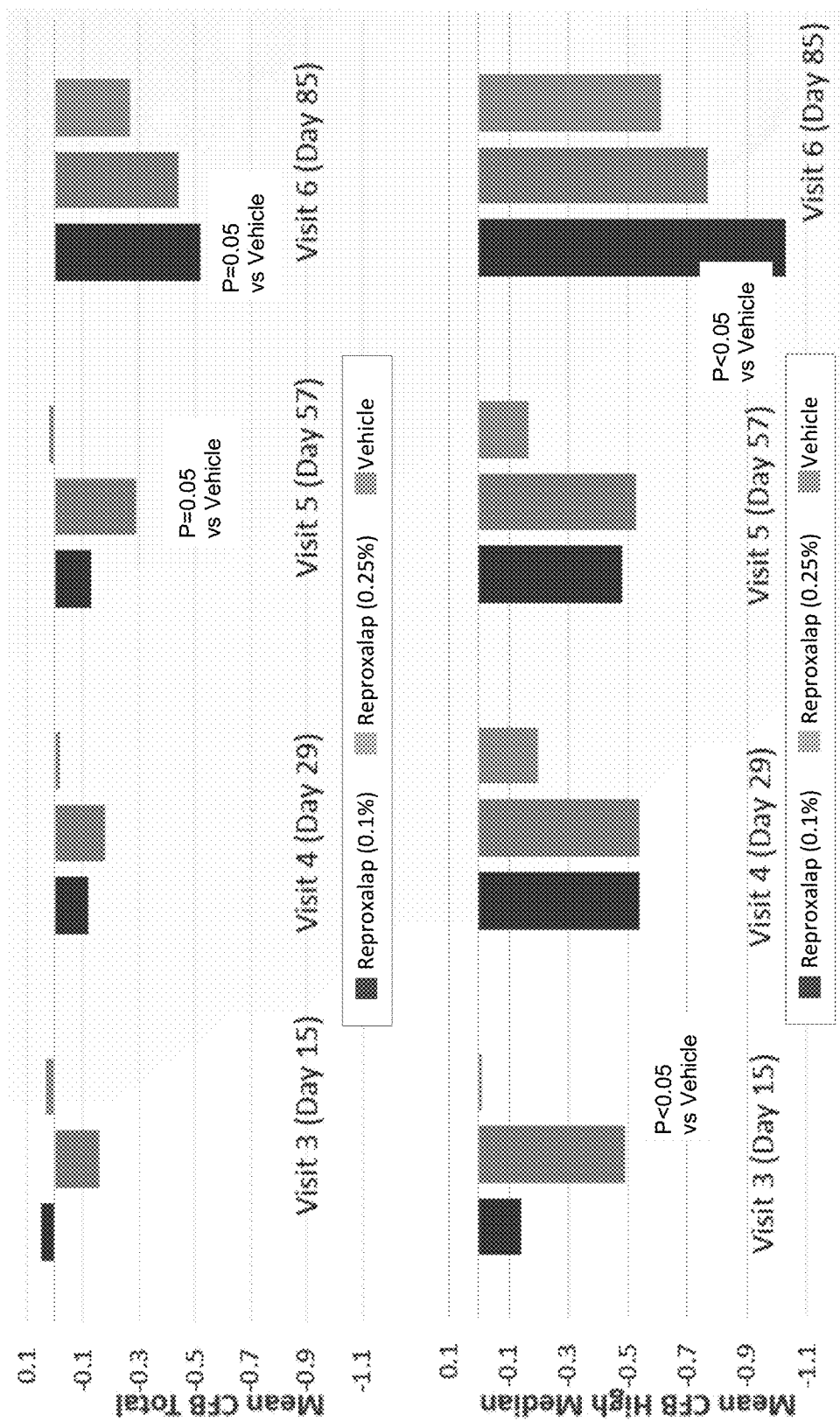
FIG. 9 depicts Fluorescein Staining: Conjunctival Sum Score (Nasal and Temporal) Total Population (N=100/100/100) vs High Median Subgroup (N=55/56/60) (ITT Population with Observed Data Only).

The phase 2b data are shown in FIGS. 1 through 9 and Tables I through 3.

Key Observations From Phase 2b Clinical Trial

1. Early onset of effect from Phase 2b evidenced across multiple signs and symptoms
   Majority (>50-100%) of effect vs vehicle seen at the first study endpoint (Week 2 or 4) in 0.25% group:
   Positive early onset for 3 out of 4 symptom endpoints: ODS, OD4SQ, OSDI
   Negative for SANDS
   Positive early onset for 3 out of 4 sign endpoints: Lissamine green total score, fluorescein total score, tear osmolarity
   Negative for TFBUT® (met definition at week 4)
   Schirmer's Test only assessed at week 12
2. Dose response was demonstrated between 0.1% and 0.25% dose strengths
3. 0.1% reproxalap matched higher dose effects at later time points
   Clearest effect with signs, especially ocular staining
   Compliance poorest in 0.25% group (8% non-compliant vs 3% in the 0.1% group and 1% in the vehicle group)
4. Vehicle effect increased with study duration
   Clearest effect was observed with signs, especially ocular staining
   Normal pattern in DED with plateau around two to three months
   QID vehicle in Phase 2b was expected to have increased this effect

TABLE 3

Phase 2b Clinical Trial Results Heat Map: Broad Phase 2a Activity Reproduced
Reproxalap Phase 2b DED Results Heat Map
Intent to Treat (ITT) Population with Observed Data Only
Non-CAE and Pre-CAE
Endpoint-Specific Worst Eye (where applicable)

|  |  |  | Drug Trend? | Dose Trend? | Reproxalap 0.1% | | | | | | Reproxalap 0.25% | | | | | |
|---|---|---|---|---|---|---|---|---|---|---|---|---|---|---|---|---|
|  |  |  |  |  | Effect Size >0.5 | vs. Vehicle p-value ANCOVA | | | | Effect Size >0.5 | vs. Vehicle p-value ANCOVA | | | | |
|  |  |  |  |  |  | V3 | V4 | V5 | V6 |  | V3 | V4 | V5 | V6 |
| Symptom Measures | | | | | | | | | | | | | | | |
| Ocular Discomfort Scale |  | (0-4) | ✓ | ✓ | ✓ |  |  |  |  | ✓ |  |  |  |  |
| OD & 4-Symptom Questionnaire | Overall Ocular Discomfort | (0-5) | ✓ | ✓ | ✓ |  |  |  | c | ✓ |  |  |  | a |
|  | Burning | (0-5) | ✓ |  |  | N/A | b |  |  | N/A |  |  |  |  |
|  | Dryness | (0-5) | ✓ | ✓ | ✓ |  |  |  |  | ✓ |  | c |  | a |
|  | Grittiness | (0-5) | ✓ | ✓ |  |  |  |  |  | ✓ |  |  |  | c |
|  | Stinging | (0-5) | ✓ | ✓ |  |  |  | b | c | ✓ |  | c |  | a |
| Ocular Surface Disease Index (OSDI) |  | (0-100) | ✓ | ✓ |  | N/A |  |  |  | ✓ |  |  |  |  |
| SANDE Questionnaire | Severity | (0-100 mm) | ✓ | ✓ |  |  | N/A |  |  | ✓ |  |  |  | b |
|  | Frequency | (0-100 mm) | ✓ |  | ✓ |  |  |  |  | ✓ |  |  |  |  |
| Sign Measures | | | | | | | | | | | | | | | |
| Lisamine Green Staining | Total Score (all five regions) | (0-20; Σ 5x) | ✓ | ✓ | ✓ |  |  |  |  | ✓ |  |  |  |  |
|  | Corneal Sum Score (Inferior, Superior, Central) | (0-12; Σ 3x) | ✓ | ✓ | ✓ |  |  |  |  | ✓ | c |  |  |  |
|  | Conjunctival Sum Score (Nasal and Temporal) | (0-8; Σ 2x) | ✓ | ✓ |  |  |  |  |  | ✓ |  |  |  | c |
|  | Inferior | (0-4) | ✓ | ✓ |  |  |  |  |  |  |  |  |  |  |
|  | Superior | (0-4) | ✓ | ✓ | ✓ |  | N/A |  |  |  | a |  | N/A | N/A |
|  | Central | (0-4) | ✓ | ✓ |  | N/A |  | N/A |  | ✓ | N/A |  |  |  |
|  | Temporal | (0-4) | ✓ | ✓ |  |  |  |  |  | ✓ |  | b |  |  |
|  | Nasal | (0-4) | ✓ | ✓ | ✓ | N/A | N/A | b |  | ✓ |  |  |  | c |
| Fluorescein Staining | Total Score (all five regions) | 0-20; Σ 5x | ✓ |  | ✓ |  |  |  |  | ✓ | b |  |  |  |
|  | Corneal Sum Score (Inferior, Superior, and Central) | 0-12; Σ 3x | ✓ |  |  |  |  |  |  | ✓ | a |  |  | N/A |
|  | Conjunctival Sum Score (Nasal and Temporal) | (0-8; Σ 2x) | ✓ | ✓ |  | N/A |  | b |  |  |  |  | b |  |

TABLE 3-continued

Phase 2b Clinical Trial Results Heat Map: Broad Phase 2a Activity Reproduced
Reproxalap Phase 2b DED Results Heat Map
Intent to Treat (ITT) Population with Observed Data Only
Non-CAE and Pre-CAE
Endpoint-Specific Worst Eye (where applicable)

| | | | | | Reproxalap 0.1% | | | | | Reproxalap 0.25% | | | | |
|---|---|---|---|---|---|---|---|---|---|---|---|---|---|---|
| | | Dose | Drug Trend? | Dose Trend? | Effect Size >0.5 | vs. Vehicle p-value ANCOVA | | | | Effect Size >0.5 | vs. Vehicle p-value ANCOVA | | | |
| | | | | | | V3 | V4 | V5 | V6 | | V3 | V4 | V5 | V6 |
| | Inferior | (0-4) | ✓ | | | | | | | | c | | | |
| | Superior | (0-4) | | | ✓ | | | | N/A | ✓ | | | N/A | N/A |
| | Central | (0-4) | ✓ | ✓ | ✓ | N/A | | | N/A | ✓ | | | | N/A |
| | Temporal | (0-4) | ✓ | ✓ | | N/A | N/A | | | | b | | b | |
| | Nasal | (0-4) | ✓ | ✓ | | N/A | | | a | | c | a | | b |
| Tear Film Break-Up Time | | (sec) | | ✓ | ✓ | N/A | N/A | | | ✓ | N/A | | | N/A |
| Schirmer's Test | | (mm) | ✓ | ✓ | ✓ | | | | | ✓ | | | | |
| Osmolarity | | (mOsm/L) | ✓ | | ✓ | | | | | ✓ | | | | |

P-value Key
P < 0.05 a
P < 0.10 b
P < 0.15 c
wrong signal^ N/A
^ wrong signal defined as an effect less than Vehicle, or a worsening vs. baseline While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

All publications, patents, patent applications and other documents cited in this application are hereby incorporated by reference in their entireties for all purposes to the same extent as if each individual publication, patent, patent application or other document were individually indicated to be incorporated by reference for all purposes.

We claim:

1. A method of treating dry eye disease in a subject, comprising topically administering to an eye of a subject with dry eye disease a therapeutically effective amount of an ophthalmic solution comprising reproxalap, or a pharmaceutically acceptable salt thereof, at about 0.2% w/v to about 0.3% w/v, and a pharmaceutically acceptable excipient comprising a cyclodextrin, wherein the cyclodextrin is sulfobutylether-β-cyclodextrin or hydroxypropyl-β-cyclodextrin, or a pharmaceutically acceptable salt thereof; wherein the reproxalap and cyclodextrin are present in a ratio of about 1:2, about 1:3, about 1:4, or about 1:5 on a mole:mole basis; and wherein the ophthalmic solution is topically administered to the eye with dry eye disease four times a day in an initiation phase or exacerbation phase followed by three times a day, twice a day, once a day, or as needed in a maintenance phase.

2. The method of claim 1, wherein the ophthalmic solution is topically administered to the eye with dry eye disease three times a day in the maintenance phase.

3. The method of claim 1, wherein the ophthalmic solution is topically administered to the eye with dry eye disease two times a day in the maintenance phase.

4. The method of claim 1, wherein the ophthalmic solution is topically administered to the eye with dry eye disease once a day in the maintenance phase.

5. The method of claim 1, wherein the treatment is for at least 12 weeks.

6. The method of claim 1, wherein the ophthalmic solution is topically administered to the eye with dry eye disease four times a day for about 2 to 6 weeks in an initiation phase or exacerbation phase followed by administration three times a day, two times a day, once a day, or as needed in a maintenance phase.

7. The method of claim 6, wherein the maintenance phase is administration three times a day, two times a day, once a day, or as needed for about 6 to 10 weeks.

8. The method of claim 7, wherein the maintenance phase is administration two times a day.

9. A method of treating dry eye disease in a subject, comprising:
topically administering to an eye of a subject with dry eye disease a therapeutically effective amount of an ophthalmic solution comprising reproxalap, or a pharmaceutically acceptable salt thereof, and a pharmaceutically acceptable excipient comprising a cyclodextrin, wherein the reproxalap is at about 0.2% w/v to about 0.3% w/v, and the cyclodextrin is sulfobutylether-β-cyclodextrin or hydroxypropyl-β-cyclodextrin, or a pharmaceutically acceptable salt thereof, wherein the reproxalap and cyclodextrin are present in a ratio of about 1:2, about 1:3, about 1:4, or about 1:5 on a mole:mole basis, and
wherein the ophthalmic solution is administered four times a day.

10. The method of claim 9, wherein reproxalap is at about 0.25% w/v and the pharmaceutically acceptable excipient comprises sulfobutylether-β-cyclodextrin, wherein the sulfobutylether-β-cyclodextrin, or a pharmaceutically acceptable salt thereof of is at about 7% w/v.

11. The method of claim 9, wherein reproxalap is at a concentration of 0.25% w/v and the pharmaceutically acceptable excipient comprises sulfobutylether-β-cyclodextrin, wherein the sulfobutylether-β-cyclodextrin, or a pharmaceutically acceptable salt thereof, is at about 11% w/v.

12. A method of treating dry eye disease in a subject, comprising topically administering to an eye of a subject with dry eye disease a therapeutically effective amount of an ophthalmic solution comprising reproxalap, or a pharmaceutically acceptable salt thereof, and a pharmaceutically acceptable excipient comprising a cyclodextrin, wherein the reproxalap is at about 0.2% w/v to about 0.3% w/v, and the cyclodextrin is sulfobutylether-β-cyclodextrin or hydroxypropyl-β-cyclodextrin, or a pharmaceutically acceptable salt thereof, wherein the reproxalap and cyclodextrin are present in a ratio of about 1:2, about 1:3, about 1:4, or about 1:5 on a mole:mole basis, and wherein the ophthalmic solution is administered at least four times a day in an initiation phase or exacerbation phase, followed by three times a day, two times a day, once a day, or as needed in a maintenance phase.

13. The method of claim 12, wherein the ophthalmic solution is administered two times a day in the maintenance phase.

14. The method of claim 12, wherein reproxalap is at about 0.25% w/v and the pharmaceutically acceptable excipient comprises sulfobutylether-β-cyclodextrin, wherein the sulfobutylether-β-cyclodextrin, or a pharmaceutically acceptable salt thereof of, is at about 7% w/v.

15. The method of claim 12, wherein reproxalap is at a concentration of 0.25% w/v and the pharmaceutically acceptable excipient comprises sulfobutylether-β-cyclodextrin, wherein the sulfobutylether-β-cyclodextrin, or a pharmaceutically acceptable salt thereof, is at about 11% w/v.

16. The method of claim 12, wherein the ophthalmic solution is administered at a dose strength to achieve an early onset of effect.

17. The method of claim 16, wherein the early onset effect is for dry eye symptoms of one or more of: ocular dryness, itchiness, tearing, burning, stinging, grittiness, cloudy vision, sensitivity to environment, and stringy ocular secretion.

18. The method of claim 16, wherein the early onset of effect is for dry eye signs of one or more of: ocular vital staining, tear film break-up time, tear osmolarity, and tear volume.

19. The method of claim 1, wherein the ophthalmic solution further comprises a tonicity agent consisting of about 0.2 to about 0.3% w/v sodium chloride, 0.07 to 0.09% sodium phosphate (dibasic), and 0.015% to 0.019% w/v sodium phosphate (monobasic); and the pH is about 7.3.

20. The method of claim 1, wherein the reproxalap and cyclodextrin are present in a ratio of about 1:3 on a mole:mole basis.

21. The method of claim 1, wherein the reproxalap and cyclodextrin are present in a ratio of about 1:4 on a mole:mole basis.

22. The method of claim 1, wherein reproxalap, or a pharmaceutically acceptable salt thereof, is at about 0.25% w/v, and the cyclodextrin is sulfobutylether-β-cyclodextrin at about 7% w/v.

23. The method of claim 1, wherein reproxalap, or a pharmaceutically acceptable salt thereof, is at about 0.25% w/v, and the cyclodextrin is sulfobutylether-β-cyclodextrin at about 11% w/v.

24. The method of claim 19, wherein the reproxalap and cyclodextrin are present in a ratio of about 1:4 on a mole:mole basis.

* * * * *